United States Patent [19]

Andreiko et al.

[11] Patent Number: 5,533,895
[45] Date of Patent: Jul. 9, 1996

[54] ORTHODONTIC APPLIANCE AND GROUP STANDARDIZED BRACKETS THEREFOR AND METHODS OF MAKING, ASSEMBLING AND USING APPLIANCE TO STRAIGHTEN TEETH

[75] Inventors: Craig A. Andreiko, Alta Loma; Mark A. Payne, Whittier, both of Calif.

[73] Assignee: Ormco Corporation, Glendora, Calif.

[21] Appl. No.: 285,942

[22] Filed: Aug. 4, 1994

Related U.S. Application Data

[63] Continuation-in-part of Ser. No. 141,376, Oct. 22, 1993, Pat. No. 5,395,238, and Ser. No. 973,973, Nov. 9, 1993, Pat. No. 5,431,562, which is a continuation-in-part of Ser. No. 775,589, Oct. 15, 1991, abandoned, and Ser. No. 875,663, Apr. 29, 1992, abandoned, which is a continuation of Ser. No. 467,162, Jan. 19, 1990, Pat. No. 5,139,419, said Ser. No. 141,376, is a continuation of Ser. No. 775,589, Oct. 15, 1991, abandoned, which is a continuation-in-part of Ser. No. 467,162.

[51] Int. Cl.⁶ ..................................................... A61C 7/00
[52] U.S. Cl. ................................................... 433/24; 433/8
[58] Field of Search ............................................. 433/24, 8

[56] References Cited

U.S. PATENT DOCUMENTS 3,660,900  5/1972  Andrews .................................... 433/24
5,011,405  4/1991  Lemchem .................................. 433/24
5,139,419  8/1992  Andreiko et al. ............................ 43/24
5,318,441  6/1994  Keller ........................................ 433/24

OTHER PUBLICATIONS

Catalog: Ormco Orthodontic Products, pub. by Ormco Corporation, 1990, Sec. 1, 2, 3 & 5.
Catalog: 3M Unitek Orthodontic Product, pub. by 3M, pp. 1–1 to 1–55, 2–1 to 2–44, 5–1 to 5–17.
Catalog: Rocky Mountain Orthodontics Cat. #4, pub. by RMO, Inc., pp. E1–E62 & G6–G9.
Catalog: Orthodontics pub. by Dentaurum, Inc., pp. 1–69, 90–98.

Primary Examiner—Cary E. O'Connor
Attorney, Agent, or Firm—Wood, Herron & Evans

[57] ABSTRACT

A computerized method of designing custom orthodontic appliances based on the individual anatomy of the individual patient is used in a further method of statistically processing the appliance design parameters to produce standardized appliances, particularly orthodontic brackets, for patient groups or classes of patients that share certain features of dental anatomy, common treatment problems or similar preferred treatment goals. Standardized brackets are provided in various combinations for patients of racial or other anthropological groups, including bracket combinations and bracket sets for Asian patients and for Caucasian patients. Methods for treating patients and providing group specific appliances to patients are also provided.

109 Claims, 4 Drawing Sheets

ORTHODONTIC APPLIANCE AND GROUP STANDARDIZED BRACKETS THEREFOR AND METHODS OF MAKING, ASSEMBLING AND USING APPLIANCE TO STRAIGHTEN TEETH

This application is a continuation-in-part of U.S. patent application Ser. No. 08/141,376, filed Oct. 22, 1993, now U.S. Pat. No. 5,395,238 entitled Method of Forming Orthodontic Brace, which is a continuation of U.S. patent application Ser. No. 07/775,589, filed Oct. 15, 1991, now abandoned, which is a continuation-in-part of U.S. application Ser. No. 07/467,162, filed Jan. 19, 1990, now U.S. Pat. No. 5,139,419.

This application is also a continuation-in-part of pending U.S. patent application Ser. No. 07/973,973, filed Nov. 9, 1993, now U.S. Pat. No. 5,431,562 Method and Apparatus for designing and forming a custom orthodontic Appliance and for the Straightening of Teeth Therewith, which is a continuation-in-part of abandoned U.S. application Ser. No. 07/775,589, identified above, and is also a continuation-in-part of pending U.S. patent application Ser. No. 07/875,663, filed 29 Apr. 1992, which is a continuation of U.S. patent application Ser. No. 07/467,162, identified above.

This application is related to the applications of applicants filed simultaneously herewith entitled "Low Profile Orthodontic Appliance", "Coordinated Orthodontic Archwires and Method of Making Same" and "Orthodontic Appliance Providing for Mesial Rotation of Molars."

The U.S. applications identified above are commonly owned and assigned to the assignee of the present application and all are hereby expressly incorporated into this application by reference.

1. Field of the Invention

The present invention relates to orthodontic appliances for straightening teeth, particularly to appliances that include sets of standardized orthodontic brackets, subsets of standardized orthodontic brackets, and individual standard orthodontic brackets for patients, and to methods of designing, providing and using such orthodontic appliances.

2. Background of the Invention

In the prior art, orthodontists have desired, and orthodontic appliance manufactures have made efforts to produce, appliances that include orthodontic brackets and other devices for mounting on the individual teeth of patients to support orthodontic archwires in such a way as to require a minimum amount of manual bending and reshaping of the wire by the orthodontist during patient treatment. In pursuit of these efforts, studies have been made of the dental anatomy of patients whose teeth lie naturally in tooth positions that orthodontists have regarded as ideal. As a result of these studies, orthodontic appliances have been manufactured that include orthodontic brackets configured to certain standardized geometric parameters that provide a selection from which orthodontists can select brackets most suitable for straightening the teeth of the individual patients to the presumed ideal finish positions in accordance with certain selected norms.

The appliances of the prior art have, however, failed to include brackets and other components most suitable for the dental anatomies of all patients whose teeth are maloccluded. This is in part because, in the prior art, orthodontic brackets have designed based on studies of tooth shapes of patients who do not require orthodontic treatment. In addition, most such patients have been Caucasian. Thus, the resulting brackets and other appliance components manufactured and made available to orthodontists have been better suited for patients having ideal dental anatomy and who are Caucasian than for those patients of other racial or anthropological groups. Furthermore, such standardized appliance components have been less than ideally suited for patients of any group whose teeth are maloccluded. As a result, such brackets and other appliance components have not been ideal even for many Caucasian patients.

Reasons for deficiencies in prior art standardized orthodontic brackets include not only the failure to adequately consider the differing dental anatomies of patients among different groups, but the inadequacy of criteria used in determining the ideal finish positions to which maloccluded teeth of patients are to be moved. The criteria include, for example, norms of individual tooth orientation angles. As used herein these include angulation ("tip") about a horizontal labial-lingual axis in the mesial (+) or distal (−) direction, tooth inclination ("torque") about a mesio-distal axis in the labial/buccal (+) or lingual (−) direction, and rotation about a vertical axis in the mesial(+, from the facial side) or buccal (−) direction.

For example, as disclosed in U.S. Pat. Nos. 3,477,128 and 3,660,900 of Andrews and 4,669,981 of Kurz, orthodontic goals have been based on achieving finish tooth positions that produce particular angles of inclination at the midpoint of the tooth surface on the facial side of the tooth ("facial axis") according to certain statistical norms for each of the respective teeth in the mouth of the patient. Such norms, originally published by Andrews in 1960 (see Lawrence F. Andrews, Straight Wire, *The Concept and Appliance*, L. A. Wells Co., 1989), were established as preferable, based on statistics most probably and generally assumed to be derived largely from Caucasian teeth in the mouths of Caucasian patients. Such norms, however, do not produce ideal tooth placement for all Caucasian patients. The concept of placing the teeth to achieve the statistically established facial inclination angles has served the orthodontist who makes treatment or appliance modification decisions, since visual observation of facial surfaces of the teeth is easily accomplished. However, because variations from the average tooth surface shapes, including the facial axes of the teeth, relative to the functional prominences of teeth of patients are common within a patient group, the use of facial measurements as a criteria can aggravate errors in the treatment of individual patients whose dental anatomies deviate from the norm.

In addition, criteria of the prior art have been based on assumptions that the dental anatomy and tooth finish positions of patients who do not need orthodontic treatment represent the ideal on which orthodontic treatment to correct malocclusions are based. As a result, orthodontic appliance components have been built to fit a statistical group of persons who may not have the tooth or jaw shapes that have, in part at least, contributed to the malocclusions that must be orthodontically corrected.

Consideration of possible dental anatomical differences among population groups, such as differences in the preferred inclinations of the facial mounting surfaces of teeth, to which brackets are most commonly attached in the course of orthodontic treatment, has resulted in an extension of the Andrews type norms to patients of other than the Caucasian group. A study to derive norms equivalent to the norms of Andrews for Japanese patients, is set forth in the study by Etsuko Sebata entitled "An Orthodontic Study of Teeth and Dental Arch Form on the Japanese Normal Occlusions", Shikagakuho (Journal of Dentistry) Vol. 80, No. 7 (1980), p. 11–35. Similarly, for Korean patients, there has been published a paper by Yound—Chel Park D. D. S., Ph.D., College of Dentistry, Yonsei University, Seoul, Korea, entitled "A Study of the Morphology of Straight Wire Brackets For Koreans" However, due to the same limitations and assumptions that have been present in studies on predominantly Caucasians, such as using the facial inclination angles of teeth as a final tooth placement criteria and studying persons whose teeth are not maloccluded, such studies alone do not lead to suitable tooth placement or orthodontic appliance design for Asian patients or patients of any other group requiring orthodontic treatment. Therefore, the goal of producing standard orthodontic appliances that will move the teeth of large numbers of the patients who need treatment to ideal positions with a minimum of manual bending of wire by orthodontists has not been achieved in the prior art.

Accordingly, there is a need to provide patients of various patient groups, such as anthropological groups, with standard orthodontic appliances that are more ideally suited to their dental anatomy than the orthodontic appliances of the prior art. Particularly, there is a need for a method of designing standard orthodontic brackets, and standard orthodontic brackets, individually and in combination, that are better suited for patients of different groups.

SUMMARY OF THE INVENTION

Applicants have determined that the orthodontic studies of the prior art that lead to the ideal tooth positioning norms are themselves based on criteria that are not sufficiently independent of anatomical variations, not only among patients of different anthropological groups, but among patients within the Causation racial group, and among patients whose anatomies and malocclusions can be otherwise classified in statistically significant groups. As a consequence, using the currently accepted norms often places the teeth in less than ideal positions. For example, as set forth in applicants' pending U.S. patent applications Ser. Nos. 07/775,589 and 08/973,973, the use of the inclination of the facial surface of the teeth to establish norms for tooth inclination or torque angle settings is less likely to produce optimal tooth placement than the use of the criteria proposed by applicants in those patent applications to improve upon the prior art.

In U.S. patent application Ser. No. 08/973,973 of applicants and those applications incorporated therein, applicants have provided for the design and manufacture of custom orthodontic appliances, including custom brackets to produce individual ideal results based on individual patient anatomy. Further, by consideration of appliance design on an individual basis, applicants have concluded that teeth will be better positioned in accordance with norms that differ from those used in the prior art approaches. For example, applicants have therein concluded that the bodily inclination of the teeth is less dependent on anatomical variations among patients than to the facial inclinations of the teeth, whether such variations are those occurring among teeth of patients classified in different groups or those occurring among patients of the same groups.

In their U.S. patent applications referred to above, applicants have provided improvements over the prior art, and particularly, have provided for the improvement of orthodontic parameters using tooth inclination seed values from which to automatically calculate ideal tooth finish position from tooth shape data derived from the individual patients. With computerized parameter improvement, applicants optimize tooth inclination angles to those ideal for the particular patient being treated. It has been particularly found by applicants by using their computerized method that considerable improvement over the norms used for tooth placement and over brackets of the prior art is required for Caucasian patients, for Asian patients, and for patients of other racial and other anthropological groups. As a result, standardized brackets that have been provided in accordance with the accepted criteria can be improved upon. Furthermore, the providing of brackets standardized for patients of specific anthropological or other groups can result in better functioning standardized appliances.

Accordingly, it is an objective of the present invention to provide standardized orthodontic appliances, and particularly standardized orthodontic brackets for orthodontic appliances, that will facilitate the achievement of the orthodontic goal of achieving ideal tooth placement faster and with the appliances with a minimum of manual adjustment, such as archwire bending or reshaping, by the orthodontist.

It is a particular objective of the present invention to provide separate standardized orthodontic appliances, particularly orthodontic brackets, bracket sets and bracket subsets, for such appliances, for patients of various anthropological groups, that will be suitable for achieving optimal tooth placement for patients of the groups with minimum intervention by the orthodontist, accommodating the dental anatomical characteristics that the members of the group have in common and that distinguish the them from members of other such groups. The term "bracket" used herein is intended to include what is known as the standard tie wing bracket, which includes a single or pair of archwire support wings upstanding from a base surface that is bonded to tooth, with the wings having an archwire slot of rectangular cross section therein. The term "bracket" used herein is also intended to include other types of orthodontic appliance components, such as buccal tubes, that for the archwire support and connection between the archwire and the teeth of the patient.

It is a more particular objective of the present invention to provide standard orthodontic appliances, particularly brackets therefor, that are particularly suitable in achieving orthodontic tooth placement objectives for patients who are of the Caucasian race, and for patients who are of the Asian race, particularly that portion of the Asian race than includes Japanese, Chinese, Korean and other nationalities having similar dental anatomy.

It is a further objective of the present invention to provide such orthodontic appliances as described above and to provide a method of matching patients of various anthropological groups with the appliances most suited for such groups.

It is an additional objective of the present invention to provide a method of designing orthodontic appliances that are appropriately standardized to facilitate the treatment of patients of identifiable anthropological groups, such as Asians, Caucasians, and other racially or otherwise anatomically identifiable groups that may have characteristic dental anatomy that distinguishes the members of the group form the members of other groups.

It is still another objective of the present invention to provide standardized orthodontic appliances that will function, when properly matched with patients of a particular anthropological group, to straighten the teeth of the patients on the basis of criteria that conform to statistical norms most widely applicable to the members of the various anthropological groups.

A general objective of the present invention is to provide standardized orthodontic appliances and a method of designing and producing such standard orthodontic appliances that are particularly suitable for patients who are members of variously defined groups of patients who share common anatomy or common malocclusion characteristics.

Certain aspects of the present invention are predicated in part upon the discoveries of applicants, made through the use of the method of their invention, that the overall shapes of the teeth of average patients, particularly of the average patients of racial and other typically orthodontically treated groups, differ from the typical tooth shapes widely assumed. In addition, differences between the finish tooth positions ideal for such average patients and the positions widely assumed to be idea also differ. Accordingly, the optimal standardized appliances for average patients, and particularly the average patients of typically treated groups of patients are not as widely assumed.

In accordance with certain of the principles invention, there is provided a method of establishing standardized appliance design for various groups of patients. The designs for the various groups are established by accumulating data of the design configurations of orthodontic appliances that are optimally designed for various patients, and then correlating the data with that of the group of which patient for which the appliance is designed is a member to arrive at the optimal standardized design for the group. Preferably, the statistics are accumulated from the computerized design of custom orthodontic appliances in accordance with the methods proposed by applicants in their U.S. patent application Ser. No. 973,973, identified above, and the applications and patents incorporated therein.

In accordance with applicants' custom appliance design method, digital dental anatomical data is taken of shapes in the mouths of patients requiring orthodontic treatment, ideal tooth finish positions for such patients are automatically calculated, and appliance connection points, such as for brackets on the teeth, and appliance geometry, such as archwire and bracket shape, are automatically derived. In accordance with the present invention, such statistics are combined with data of the identity of the group of which the patient is a member and of which the patient's dental anatomy is likely to be similar. Such statistics are then used to derive a statistically average design that is most likely suitable for the largest number of members of the group.

Further in accordance with the principles of the present invention, there are provided standardized appliance designs for a plurality of patient groups. Particularly provided are standardized appliances for patients generally grouped on the basis of anthropological or racial similarity. Specifically provided herein are standardized orthodontic appliances for Caucasian patients and standardized appliances for Asian patients. The appliance designs preferably include a set of orthodontic brackets more suitable for substantially all members of the group than are the appliances otherwise available from the prior art.

Further, it is contemplated that the method of design the standardized appliances be used to establish standardized appliances for other groups or subgroups, including for subgroups of the Asian and Caucasian groups as specifically provided herein. For example, it is contemplated that improved standardized appliances could be separately designed for patients of Malaysian or Indonesian subgroups that are even better suited for such subgroups than standardized appliances particularly optimized for Asian patients that include those of Japanese, Chinese and Korean subgroups of Asian patients.

Each standardized set of brackets includes, preferably, a set of twenty, twenty-four or twenty-eight brackets, including an upper subset of ten brackets for the ten upper teeth of the patient forward or mesial of the molars, and a lower subset of ten brackets for the ten lower teeth of the patient mesial of the molars. Each subset may also include two brackets for the respective first molars, and may further include two brackets for the respective second molars. Each of the upper and lower subsets includes a right side half subset of five brackets, each having a configuration specifically designed for one of the teeth, including central, lateral, cuspid, and first and second bicuspid, and also preferably first and second molars, on the respective side of the patients' mouth. Preferably, the brackets for each of the teeth on one side of each dental arch is a mirror image of the bracket for the corresponding tooth on the opposite side of the same dental arch.

Further in accordance with the present invention, the brackets of the sets each have specific standardized geometry for a particular tooth of a patient of a specific group. While each bracket, band or other component is subject to some deviation to the specific designs provided, relative dimensional parameters between brackets of a set, and particularly between brackets of adjacent teeth, are particularly established for standardization of the brackets for various patient groups.

In accordance with the preferred embodiment of the present invention, certain brackets are provided having unique and novel geometries that are particularly suited for use on specific teeth of patients of specific groups, particularly in combination with other specified brackets on other teeth of the patient, more particularly, between brackets on adjacent teeth.

Further in accordance with aspects of the present invention, the bracket geometries are designed to combine with an archwire of a low profile arcuate shape to form an overall orthodontic appliance that is also of the lowest practical profile. In addition, the appliances formed with the brackets provided in accordance with the invention are of a design that will move the teeth in accordance with norms that move the teeth to finish positions that are optimized for the groups of patients for which the brackets are standardized to criteria for the torque or inclination angle of the teeth that is based the orientation of the crown long axes of the teeth.

Also in accordance with the present invention, individual brackets and combinations of brackets and other appliance parts are selected for use on specific teeth of patients of specific anthropological or other groups by correlating the bracket designs of the present invention with data corresponding to the group of which the patient is a member.

Further in accordance with the principles of the present invention, the archwire supports of brackets or bands of standardized appliances are configured to function ideally with the brackets or other components mounted on the teeth of the patient generally to support an archwire in an archwire plane spaced from the occluding surfaces of the teeth to function optimally while avoiding interference throughout the treatment process.

The standardized appliances of the present invention provide for faster and more accurate orthodontic placement of teeth and minimize the amount of time and manual manipulation and wire bending required of the orthodontist when provided to patients of designated anthropological and other treatment groups in accordance with the present invention. Particularly, the present invention provides brackets of an designated Asian set of brackets that are better suited for patients of the broader Asian group than are brackets of the prior art, and provides brackets of a designated Caucasian set of brackets that are also better suited for patients of the broader Caucasian group than are brackets of the prior art.

These and other objectives and advantages of the present invention will be more readily apparent from the following detailed description of the drawings and preferred embodiments, in which:

DETAILED DESCRIPTION OF THE PREFERRED EMBODIMENTS:

In the design of standardized, group-specific brackets for an orthodontic appliance in accordance with the preferred embodiment of the present invention, the most accurate data of tooth shape of persons of the group is desirable. Applicants have accordingly generated data in the course of the use of the invention disclosed in their U.S. patent application Ser. No. 07/973,973, filed Nov. 9, 1993, entitled "Method and Apparatus for Designing and Forming a Custom Orthodontic Appliance and for the Straightening of Teeth Therewith", incorporated by reference above. That application describes in detail a method by which custom orthodontic appliances are designed based on individual patient anatomy. In the course of designing such appliances, the applicants have, for purposes of the present invention, generated data of the geometries of the brackets and archwires of custom orthodontic appliances along with data from which the group to which the patients belong can be determined and correlated with the derived ideal bracket and archwire geometries. The method of designing the ideal custom appliances is set forth in detail in that application, the portions of which are pertinent to the present application are summarized here.

Figure 1:
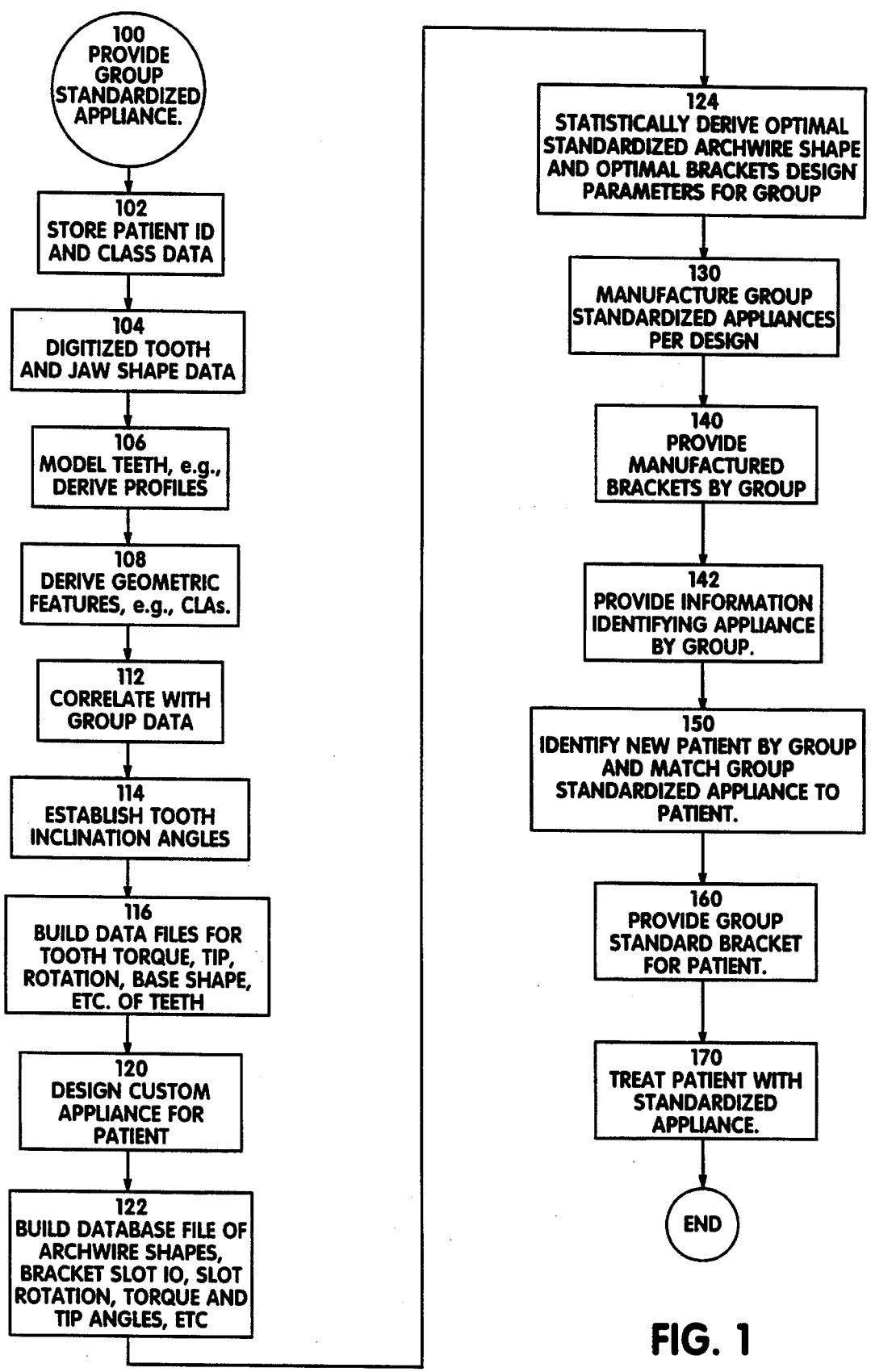
FIG. 1 is a flowchart of a method for designing optimized standardized anthropological group specific orthodontic appliances according to principles of the present invention.

The flowchart of FIG. 1 sets forth a method (100) that includes steps performed in a programmed digital computer and by certain manual steps, the numbers of which are referred to by parenthetical numbers in the related description below. In the method, the designing and manufacturing and use of the group standardized appliances begins with the computerized design and manufacture of custom orthodontic appliances, which is preceded by (102) the storing of classification data which can be used in identifying the group of which the patient is a member, such as data recording the race, sex and other data that would be helpful in determining the anthropological group to which the patient belongs. Such group may be determined at a later time, based on correlations of data of patient dental anatomy, to thereby define the group to which the patient belongs along with other patients having, for example, similar tooth and jaw shapes. Groups may also be defined as those patients whose teeth are maloccluded and require orthodontic straightening, or those having particular malocclusions or having or requiring specific orthodontic treatment, such as extractions. In any event, applicants have concluded that it is preferable that (104) anatomical shape data be gathered from patients requiring the orthodontic treatment for which the appliances are being designed rather than from persons whose occlusions are ideal.

For the individual patient from whom the classification data was taken, the design of the appliance begins by making a digital representation of each of the teeth of the patient, and preferably also of the shape of the patient's lower jaw bone. The digitization may be in the form of a full three dimensional model or the data collection may be selective. In either event, it is preferred that (106) the data be processed to produce simplified models of the patient's teeth. Such simplified models are preferably in the form of profiles of the patient's teeth, viewed mesio-distally, that is, viewed from the mesial side of the tooth and looking in the distal direction along the arch of the teeth of the respective jaw. Examples of such profiles are illustrated in FIG. 2 for the teeth mesial to the molars.

Figure 2:
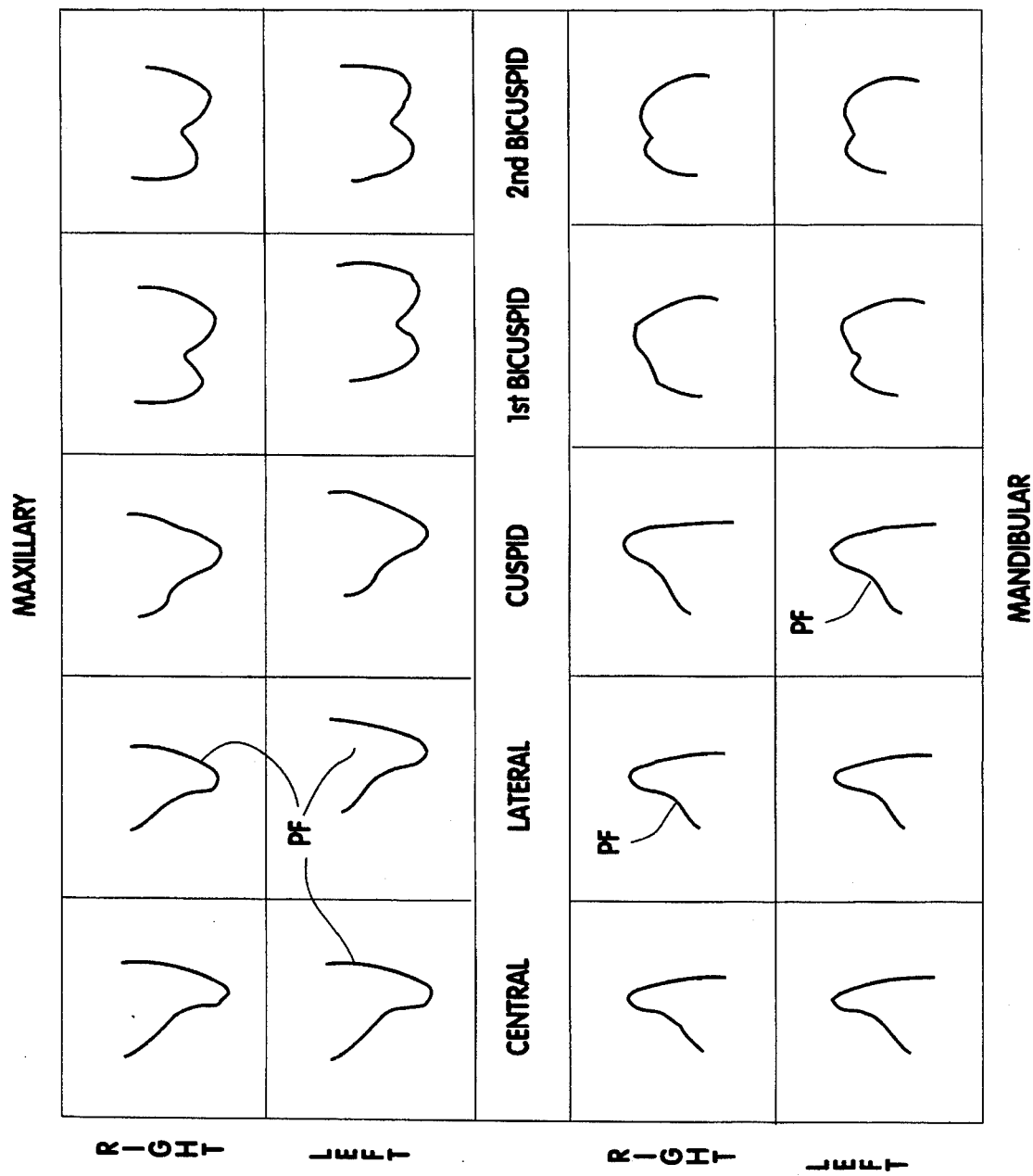
FIG. 2 is diagram of twenty vertical labial-lingual profiles each representing tooth shape characteristics of a patient in the method of FIG. 1.

Referring to FIG. 2, such profiles PF are generated for each of the teeth of the patient. The profiles may be generated by mechanically scanning a cast of the patients teeth made from a mold of the patient's upper and lower jaws, or digitally scanning a computerized model of the teeth, in a vertical labial-lingual plane, or in a way that will otherwise pick up the prominences of the tooth that are most relevant to how the teeth fit in the mouth and how different teeth occlude. The resulting profiles may be cross-sections of the teeth in the vertical labial-lingual planes that bisect the teeth, but, for multi-cusped teeth, are preferably symbolic profiles that each resemble a projection of the tooth on such a plane, and containing lingual and buccal cusp tips of the tooth as well as the position of the central groove and/or marginal ridge and the positions of the buccal and lingual gingival contact points of the tooth crown.

Figure 2A:
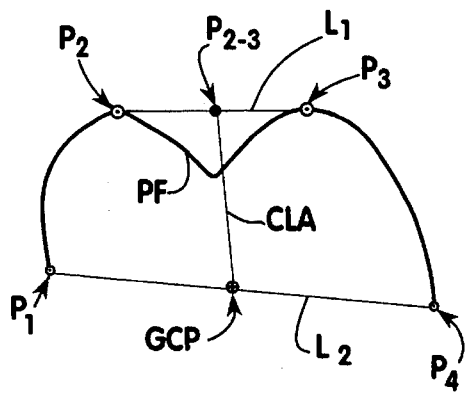
FIG. 2A is diagram of a tooth profile, from those of FIG. 2, for a lower posterior tooth.

For most calculation purposes, the profiles PF may be in the form of simplified mathematical models that treat the teeth for many calculations as labial-lingually extending vertical planar objects bisecting the mesio-distal widths of the teeth and containing a line that may be defined as the crown long axis of the tooth. Profiles are diagrammatically illustrated in FIG. 2A as examples for lower molars or bicuspids, in FIG. 2B for lower incisors or cuspids, in FIG. 2C for upper molars or bicuspids and in FIG. 2D for upper laterals or centrals. These profiles are constructed in a computer from the digitized information of the tooth shape for each tooth.

Once constructed, (108) a line is derived representing the crown long axis CLA of the tooth that is representative of the bodily center of the profile of the tooth in the labially-lingually extending plane. The CLA is derived by defining four points on the profile. On the anterior teeth (FIGS. 2B and 2D), the points include the lingual contact point $P_1$ on the profile of the crown with the gum, a point $P_2$ on the lingual side of the incisal tip, a corresponding point $P_3$ at approximately the same height on the labial side of the incisal tip and the labial contact point $P_4$ on the profile of the crown with the gum. Then, a line $L_1$ is constructed between points $P_2$ and $P_3$, a line $L_2$, is constructed joining points $P_1$ and $P_4$, and the midpoints of the lines $L_1$ and $L_2$ are determined and defined respectively as the incisal center point ICP and the gingival center point GCP. The CLA is defined as a line constructed through GCP and ICP.

Figure 2B:
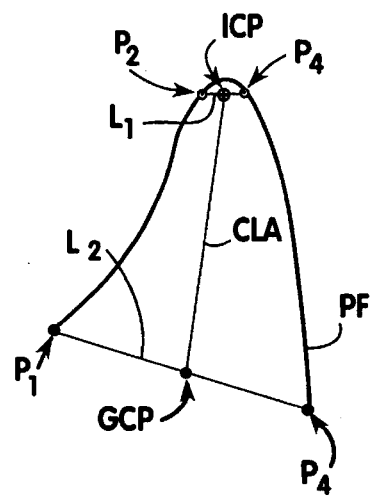
FIG. 2B is a diagram similar to FIG. 2A of a lower anterior tooth.
Figure 2C:
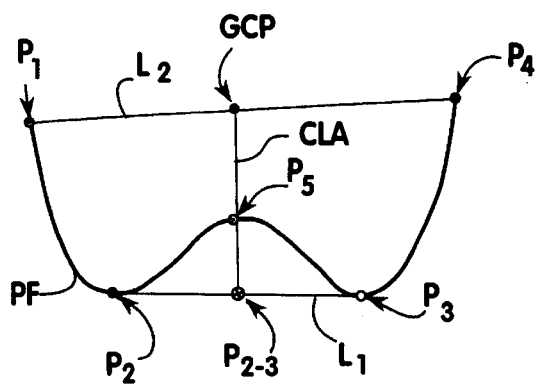
FIG. 2C is a diagram similar to FIG. 2A of an upper posterior tooth.
Figure 2D:
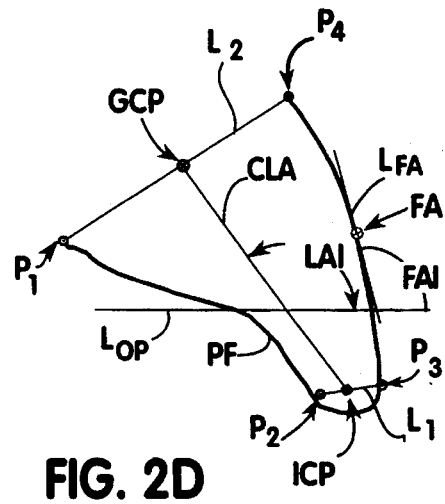
FIG. 2D is a diagram similar to FIG. 2A of an upper anterior tooth.

For posterior teeth, a line representing the crown long axis CLA of the tooth is similarly derived by defining four points on the profile PF. Referring to FIGS. 2B and 2D, the points include the lingual contact point $P_1$ on the profile PFof the crown with the gum, the tip $P_2$ of the most prominent lingual cusp, the tip $P_3$ of the most prominent buccal cusp and the labial contact point $P_4$ on the profile PF of the crown with the gum. Then, a line $L_1$ is constructed between points $P_2$ and $P_3$, a line $L_2$, is constructed joining points $P_1$ and $P_4$, and the midpoints of the lines $L_1$ and $L_2$ are determined and defined respectively as a virtual center point $P_{2-3}$ and the gingival center point GCP. The CLA is defined as a line constructed through GCP and $P_{2-3}$.

In their custom appliance designing method, applicants' use the CLAs, as defined above, as a reference or criteria for setting the inclination or torque angles of the teeth in the calculations of the ideal finish positions of the teeth, and accordingly, in the design of the custom appliance to produce those ideal finish positions. In the treatment practiced by orthodontists in the past, the inclination of the facial surfaces of the teeth, rather than the inclination of the CLAs, has been used. The two approaches are related for any specific tooth, as can be best understood by reference to FIG. 2D. The relationship is valid and can be drawn for statistically average teeth.

Illustrated in FIG. 2D is an upper anterior tooth, for example, a cuspid, diagrammatically represented as viewed from the mesial side in the distal direction, in its ideal finish position relative to a nominally horizontal plane, represented by the line $L_{OP}$ that is parallel to a plane that may be considered to represent a plane of occlusion between the upper and lower teeth. In studies published by Andrews in 1960 and as referred to in his U.S. Pat. Nos. 3,477,128 and 3,660,900, ideal inclination or torque angle of the teeth has been defined as a facial angle of inclination FAI. The angle of inclination FAI is defined, according to Andrews, by determining the facial axis of the tooth, which is a line FA perpendicular to the labial or buccal surface of the tooth at the vertical midpoint FC of the tooth between the incisal center or tip of the tooth IC and the gingival center point of the tooth, which may be represented as applicants' point $P_4$. Through the point FC, a line $L_{FA}$ is defined tangent to the surface of the tooth, perpendicular to the line FA. The facial inclination angles FAI formed by such a line $L_{FA}$ with the such a plane $L_{OP}$ were tabulated by Andrews for patients whose teeth are naturally in positions regarded as ideal. Andrews tabulated these angles FAI from data taken from, what he termed, 120 Optimal Occlusions. Orthodontists have adopted such tabulated angles as a criteria by which the maloccluded teeth of patients needing orthodontic treatment should be ideally positioned. In addition, it is generally believed that the data of Andrews was taken from patients in the United States who, while not specifically classified, were probably predominantly Caucasian.

From the ideal angle FAI for each respective tooth, it can be appreciated from FIG. 2D that for any given angle FAI, a value for an inclination angle of the CLA with respect to the line $L_{FA}$ can be calculated, based on the profile and the points $P_1$ through $P_4$. Accordingly, from the data taken by applicants from the analysis of a large number of uses of their custom appliance designing method, average tooth profiles have been statistically derived and the relationship of the CLA to the $L_{FA}$ determined for each tooth. Then, the ideal inclination of the tooth, as previously described in terms of the angle FAI, was tabulated by applicants in terms of the angle LAI for the statistically average maloccluded tooth. This angle is described by applicants in their prior U.S. patent applications Ser. Nos. 07/775,589 and 07/973,973 incorporated by reference above.

As is discussed elsewhere herein, (112) before calculating ideal inclination angles in terms of CLA, applicants group the profile data by similarity of profile shapes and correlate this data to the anthropological or other group based data of the patients to anatomically classify the patients by group. Accordingly, as described below, (114) the separate inclination angles LAI are provided by applicants for each such group. Set forth below are such angles for the anthropological or racial groups of Caucasian patients and of Asian patients.

Because applicants' custom appliance designing method is capable of precisely determining ideal finish positions for the teeth of an individual patient based on a variety of orthodontic criteria, the precalculated ideal CLAs may be employed only as seed values which the software of the custom appliance designing method improves upon by making adjustments. The ability of applicants' custom appliance designing method to optimize parameters such as the CLA inclination angles is, in one alternative, allowed to proceed automatically. In another alternative, the method accumulates data of computer suggested optimization of the inclination angles, and their values are periodically altered at the command of an operator based on experience and judgment. Automatic computer optimization is an effective way to achieve functional optimization of occlusion and tooth fit, or to achieve other tooth placement objectives that can be expressed as algorithms.

Applicants' utilization of LAIs or operator optimized tooth inclinations is as effective as were the use of FAIs to achieve aesthetic considerations. Usually, the facial characteristics of different groups influence the criteria employed in determining what the ideal tooth inclination is for a particular group. The inclination angles produced by applicants are usually not the same as those that would result if traditional FAI values were merely replaced by corresponding LAI angles for the teeth, except for patients with teeth of precisely average shapes. The calculated inclination angles and other data from the individual case analyses is collected and correlated into anthropological or other defined groups. In any of the approaches to determining the inclination to sought for the teeth, however, applicants' appliance geometry differs from those of the prior art in several other respects. One reason for such differences is due to the mounting of brackets by applicants at points on the teeth that differ from those considered in the Andrews studies and preferred. Another is due to differences, other than in tooth inclination setting, in tooth positioning criteria. Applicants have produced improved tooth positioning norms, including inclination angle establishing criteria, which differ significantly from what is conventional. The appliances produced by applicants are also different. Set forth below are such appliances of applicants for the Caucasian and Asian patient groups.

Applicants are providing a method of orthodontic treatment by which teeth are inclined to torque angles based on the CLAs, particularly as defined above, rather than by the FAIs of the prior art. From applicants' statistics discussed above, this has been found superior and less likely to be affected by deviations from the averages among patients of any group in tooth thicknesses. Therefore, a superior orthodontic treatment result is produced. The optimized CLA values, along with the statistically average profiles for the respective patient group, are used in the design of the group standardized appliance embodied in the brackets of the Caucasian bracket set described below.

Figure 3:
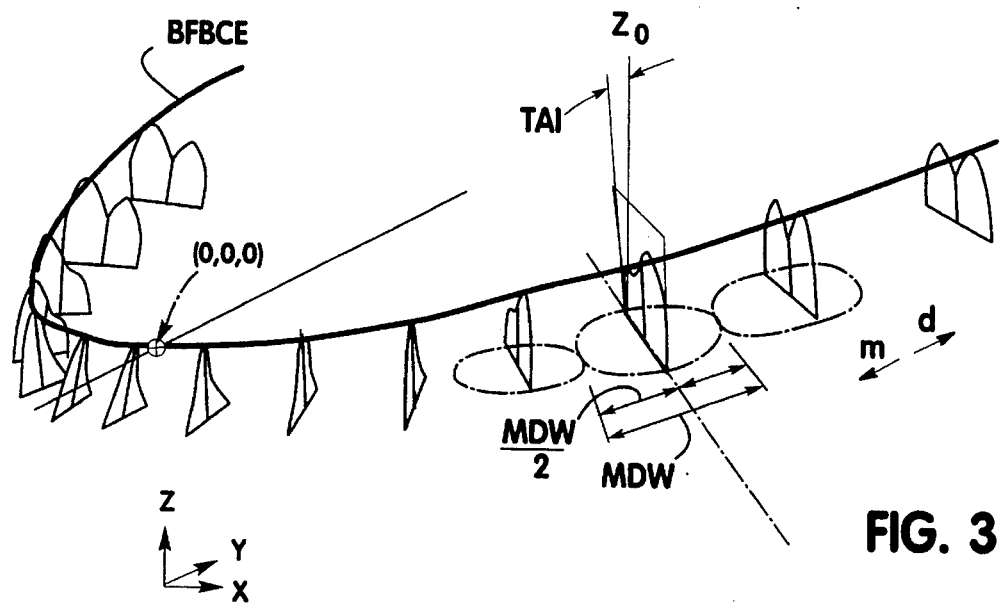
FIG. 3 is a perspective diagram showing symbolic representations of mandibular teeth arranged on a mathematical archform.

Each of the individual custom appliance designing and manufacturing cases includes the (116) calculation of ideal finish positions for the teeth of the specific individual patients, based on the specific individual anatomy of the patient, and result in certain data of position and orientation of each of the teeth of the patient with respect to a calculated and digitally defined archform that is ideal for that patient. In the design of ideal standardized brackets, such data include, in addition to the specification of the torque or inclination angles that are related to the CLAs, the establishment of preferably at least four other parameters. These additional parameters include the "tip" angle or angulation of the tooth, the "rotation" angle of the tooth, the slot in-out dimension, and the bracket base curvature. Additionally, the parameter of the location of the bracket placement position on the tooth is also provided. The tip angles of the teeth can be best understood by reference to FIG. 3. Referring to FIG. 3, a perspective diagram of a computerized mathematical model of ideal tooth finish position is illustrated, by way of example, for the mandibular teeth. The model may be taken to include some form of archform equation, for example, the equation that applicants refer to as the best fit buccal cusp equation, or BFBCE. This equation is a smooth arcuate curve on which, ideally according to applicants' theory, the incisal tips of the mandibular anterior teeth, the buccal cusp tips of the mandibular bicuspids, and the mesial buccal cusp tips of the mandibular molars are preferably placed. In relation to the equation BFBCE, the finish positions of the teeth may be defined, for example, by placing the tips of the mandibular incisors and the tips of the mesial buccal cusps of the teeth on the equation BFBCE, with the teeth inclined at the LAIs established above. This is accomplished, in the diagram of FIG. 3, by assuming that each of the teeth is capable of being defined by an individual tooth model composed of the tooth profile as representing the cross-section of the tooth in a vertical labial-lingual plane, with the profile spaced by one-half of the mesio-distal width MDW of the tooth from the contact points of the tooth with the adjacent teeth along the arch defined by the equation BFBCE. As for the maxillary teeth, they are similarly arranged relative to the BFBCE by locating the maxillary teeth relative to the points thereon that occlude with the parts of the mandibular teeth that are placed on the BFBCE.

In FIG. 3, the tip angle of the tooth is illustrated by an ideal angle TAI, that represents the angle of the plane containing the profile with respect to the vertical $Z_0$, as shown with respect to the second bicuspid. This may be viewed as a pivoting of the profile plane containing the CLA about a horizontal labial-lingual axis for the tooth LLA. This tip angle, sometimes referred to as the crown long axis angulation angle, is an established criteria for setting tooth tip angle. Applicants use, as the ideal tip angles for many of the teeth, angles obtained by from studies such as those of Andrews referred to above, with certain exceptions set forth in the data below.

The parameters defined thus far from the above description include the torque or inclination angle of the teeth, measured between a horizontal plane and the crown long axis of the tooth in the profile plane, and the angulation or tip angle, measured between the horizontal plane and the profile plane. These angles are parameters of the teeth, and from these angles the torque and tip angles of the slots of the brackets still must be derived. With respect to the third angle, the angle of rotation of the slot in the bracket, the calculation is more direct.

In tooth finish position determination, the teeth are generally oriented about their vertical or crown axes such that their profiles, such as those shown in FIGS. 2A–2D, are perpendicular to the archform equation BFBCE, with the mesial and distal contact points MCP and DCP of each respectively in contact with the distal and mesial contact points of the adjacent teeth of the same arch. The exception to this is that the centrals of each arch have their mesial contact points in contact with each other on the centerline ML of the arch. Preferably, the finish positions of the teeth are symmetrical about such centerline ML.

The determination of tooth rotation for the molars is preferably determined by the method set forth in applicants' copending U.S. patent application entitled Orthodontic Appliance Providing for Mesial Rotation of Molars. In that method, the maxillary first molar is placed first to occupy the least space on the upper dental arch. This is achieved by rotating the tooth such that the embrasure line is perpendicular to the dental archform. Then, the a line between the mesial marginal ridge and the distal lingual cusp is defined and its angle with the archform is measured. This angle is used to set the rotation of the lower first molar, by placing a line through the mesial buccal cusp tip and distal lingual groove of the lower first molar at such angle. Then the lower second molar is placed at a rotation that places both of its buccal cusps on the archform equation. Then a second angle is measured between the archform equation and a line joining the mesial buccal cusp and the distal lingual groove of this lower second molar. This second angle determines the rotation angle to which the final tooth, the upper second molar, is placed, with a line through its mesial marginal ridge and distal lingual cusp set at this second angle relative to the archform equation.

With the teeth positioned as described above, (120) the automated custom appliance designing and manufacturing method of applicants produces an appliance to achieve the calculated tooth finish positioning. To produce the treatment result of moving the patients teeth to the ideal calculated finish positions, (122) parameters such as slot torque or inclination angle, slot tip or angulation angle, slot rotation angle, slot in-out dimension, bracket base curvature and bracket placement position must be defined in terms definitive of hardware geometry. These parameters take into account the calculated tooth finish positions, the digitized shapes of the teeth and the shape of the applicants' archwire.

Figure 4:
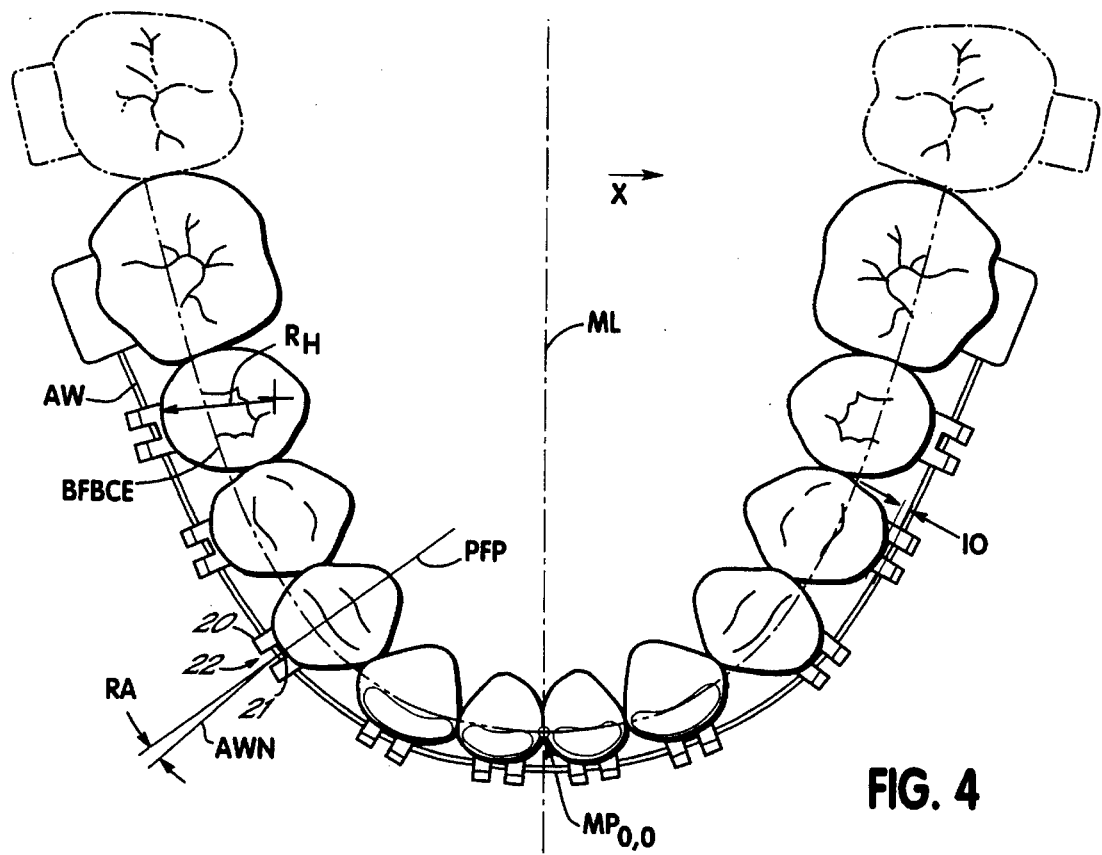
FIG. 4 is a plan view of mandibular teeth positioned on an archform with an standardized orthodontic appliance positioned thereon.

The bracket slot rotation angles will be best understood by reference to FIG. 4, which is a top view diagram of teeth that have been placed in ideal finish positions. The rotation angle for each bracket is preferably derived from data collected by use of the custom appliance design method and low profile appliance referred to above, which calculates the geometry of archwires and brackets for each individual patient. As with the custom brackets, (124) standardized optimum archwire shape data is statistically derived by correlating the calculated shapes with the anthropological group to which each of the patients belong for each custom designed appliance. For the brackets, a resulting standardized archwire AW, as shown in FIG. 4, which is in the form of an arcuate equation which is related to the dental archform equation BFBCE of FIG. 3, intersects each of the profile planes PFP to define some rotation angle RA relative to a normal line AWN perpendicular to the archwire at its intersection with the profile plane.

The archwire AW may be said to lie in an archwire plane AWP. Generally, the profile planes PFP for each tooth may be considered to be normal to the surface of the tooth in the archwire plane, and that the angle between the archwire and the surface of the tooth is the same as the angle between the archwire and the base of a bracket 20 mounted on the tooth surface at the intersections of the profile plane PFP and the archwire plane AWP. However, where data collected indicates a general deviation from that normal orientation for a particular tooth, any statistically prevalent angle between the tooth surface and the archform may be added to the angle of the archwire relative to the profile plane PFP in deriving the angle RA. This is the case with certain of the molars.

The angle RA is the rotation angle of the base 21 of the bracket slot 22, as illustrated in FIG. 4, relative to a horizontal tangent to base 25 of the bracket 20 (see FIG. 7), which mounts on and is parallel to the tooth surface at the intersection of the archwire plane AWP and the profile plane PFP at the surface of the tooth. The slot base 21 may be straight or have a slight curve to conform to the shape of the archwire, in which case the angle RA is measured with respect to a line tangent to the curve at the profile plane PFP. In determining the ideal shape of the standardized archwire AW for a population group, the shape may be derived using the custom orthodontic appliance design method of U.S. patent application Ser. No. 07/973,973 in conjunction with the determination of the lowest profile appliance, as described further in U.S. patent application of applicants, entitled Optimally Low Profile Orthodontic Appliance, filed simultaneously herewith. Such an archwire is designed to an optimized shape calculated in conjunction with the design of the brackets 20 so that the wire remains as close to the surfaces of the teeth as possible, beyond a minimum clearance of about 0.013 inches, and with a minimum of curvature change and inflection in the shape of the archwire AW. The rotation angles RA in the bracket slots 22 contribute to the achievement of the low profile appliance.

The optimally low profile appliance includes an archwire that is not necessarily mathematically similar or parallel to the ideal dental archform that will be defined by the finish positions of the teeth. The archwire is not parallel to such dental archform at every point. Preferably, such an archwire is mathematically definable by segments having curvatures and foci that differ from those of corresponding segments of the dental archform of the patient. The low profile appliance includes brackets having optimally low profiles even those that are to be mounted on smaller ones of the teeth. As a result, low profile brackets are provided for the anterior teeth, particularly the lower anterior teeth, and the archwire portion of the appliance conforms to an archform that converges with the corresponding dental archform and lies close to the teeth of the patient at the front of the patients mouth. The convergence of the archwire and the dental archform is accompanied by the provision of brackets that may be positioned and oriented on the teeth to horizontally extend perpendicular to the dental archform of the patient, but not necessarily to extend perpendicular to the archwire. Thus, the bottoms of the slots in the brackets are inclined at angles with respect to the bracket mounting surfaces of the teeth. Such angles are referred to herein, as in the practice of orthodontics, as "rotation" angles of the archwire slots of the brackets. Preferably, the slot bottoms in the bracket are curved in the archwire plane to conform to the curvature of the archwire along its length of its contact with each of the individual brackets, In defining parameters such as bracket slot rotation angle, the angle may be defined in relation to the angle of an archwire supported in the bracket slot, or in terms of the boundaries of the slot itself in the bracket. Where a snugly fitting archwire is used, that is one that is nominally the same size as the archwire slot in the bracket, these angles are approximately the same. Such exact size wires are used in applicants' custom appliance designing and manufacturing method discussed above, and may be preferred where the orthodontist has confidence in the design of the appliance for the particular patient being treated. The exact size wire would be nominally an 0.018 inch wire for use in a 0.018 inch bracket slot, or a 0.022 inch wire for use in a 0.022 inch slot. Otherwise, orthodontists may prefer somewhat smaller cross-sectioned wires, known as full size wires or small size wires. Full size wires might be nominally an 0.017 inch wire for the 0.018 inch slot bracket and a 0.021 inch wire for use with the 0.022 inch slot bracket. The small size wires might be 0.016 and 0.019 inches, respectively. The wires are rectangular in cross-section. Dimensions of full size wires, in thousandth of an inch are typically 17×25 and 21×25 respectively, while small sizes wires might be 16×22 and 19×25, respectively.

Because of the use of undersize wires, the angle of the bracket slot is not always equal to the angle of the wire being supported. However, because with the standardized appliance, it can be appreciated that certain teeth are almost always maloccluded in the same direction, and thus will be usually be urged in the same direction toward their finish positions, certain angular amounts can be added to certain bracket slot angles to render the bracket equivalent, for support of undersize wires, to a slot of given geometry for supporting exact size wires. For slot rotation angles, this additional angle may not be significant with wires tightly ligated to bi-wing brackets, but may be apparent in buccal tubes which are frequently mounted on molars. Such an additional angle may be −2° for full size wires, resulting in a closer spacing of the mesial end of the slot from the tooth than with exact size wires.

Figure 5:
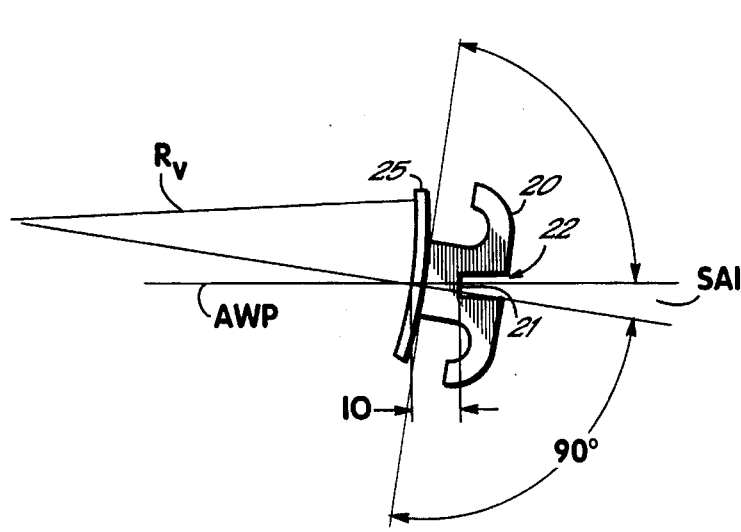
FIG. 5 is a side elevational view of a standardized orthodontic bracket and depicting the geometric parameters of a bracket according to certain embodiments of the present invention.

The inclination or torque angle LAI discussed above was defined as the torque angle of the tooth, or inclination of the tooth in the profile plane. In order to determine the geometry of the bracket slots 22, a corresponding slot angle inclination angle SAI is established, as illustrated in FIG. 5. The slot inclination angle SAI represents the angle of the slot relative to the base of the bracket that mounts to the surface of the tooth. Thus, the angle SAI is related to the tooth long axis inclination angle LAI of the group average for such tooth by the addition to the LAI of 90° plus the angle between the LAI and a vertical line in the profile plane that is tangent to the surface or profile of the tooth at the point of intersection between the profile of the tooth, when in its ideal finish position, and the archwire plane AWP. Where the bracket is to be placed at the facial axis point, as prior practice suggested, the tangent line is the line $L_{FA}$, which is inclined at the angle FAI to the archwire plane AWP of FIG. 1, as illustrated, for example, in FIG. 2D. Preferably, however, the lower archwire plane AWP is positioned at a position that is statistically determined by applicants' custom appliance design method so as to be high enough on the teeth for the appliance to apply forces and moments to the teeth effectively but being low enough to insure clearance between the appliance and the overlapping upper teeth as the teeth approach their finish positions. Thus, the vertical tangent line at the intersection of the tooth profile with the archwire plane AWP may be at an angle that differs from the FAI. Further, it is preferred that the archwire plane be approximately parallel to a plane of occlusion, represented in FIG. 4, for example, by the line $L_{OP}$. For the upper archwire plane $AWP_U$, the placement is preferably achieved that spaces the wire from the plane of occlusion, which is preferably at the level of the marginal ridge on the molars and bicuspids, and the FA point on the upper centrals. This typically results in an upper archwire plane that is sloped toward the plane of occlusion by an angle (UA of about 5° at the front, Additionally, statistics derived from the custom appliance designing method provide profile curve data for the curvature of the tooth at the point of intersection of the archwire plane AWP and the profile of the tooth, which is the point of connection of the bracket to the tooth. This curvature is established as the ideal curvature of the standardized brackets for the particular patient group. The curvature of the profile at this point of connection becomes the curvature of the bracket base in the vertical direction, as defined by a radius of curvature $R_V$ in FIG. 5. This may be a spherical curve in which both the horizontal and the vertical radii and equal, or may be a compound curve, for example, where the curvature in the horizontal or archwire plane differs from the curvature in the vertical profile plane. The horizontal radius of curvature may be represented by a radius $R_H$ as illustrated in FIG. 4. This bracket base curvature, for a flat base, will have both radii $R_V$ and $R_H$ equal to infinity; for a cylindrically shaped base, one of the radii will equal infinity and the other will have some finite radius of curvature of usually one half inch or less, a radius of much larger than one half inch being effectively infinite. Furthermore, for some teeth of some patient groups, the surface of the tooth at the bracket connection point may be concave, and thus represented by a radius that is negative. For purposes of discussion herein, such a negative radius, unless much shorter than about one half inch (i.e., $-0.5<R<0$ inches), may be considered in some contexts being equivalent to a convex radius that is "larger than" some large positive value of, for example, one half inch.

Further, as illustrated in FIG. 4 and FIG. 5, the bracket slot in-out dimension IO, preferably statistically derived from data taken in the application of applicants' custom appliance design method, further defines the limits, by patient group, of slot depth.

From the above, (124) for each patient group, five parameters are provided by which standardized brackets are designed. These include the bracket slot in-out dimension IO, the bracket base curvature R, which may include two different components $R_V$ and $R_H$, and three slot angles that include the slot inclination or torque angle SAI, the slot angulation or tip angle TAI, and the slot rotation angle RA. With these five parameters, the geometries of the brackets of respective sets of standardized brackets are defined for each of a plurality of patient anthropological groups.

Figure 6:
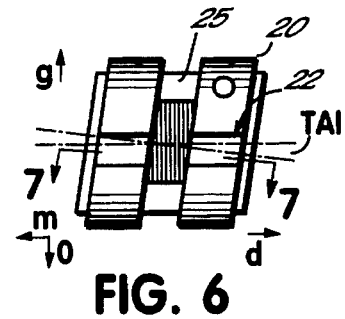
FIG. 6 is a front elevational view of the bracket of FIG. 5.
Figure 7:
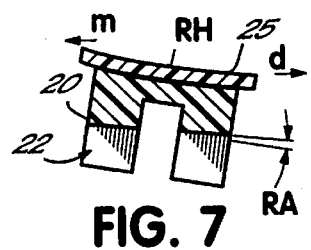
FIG. 7 is a cross-sectional view of the bracket of FIG. 6 along line 7—7.

FIGS. 5, 6 and 7 illustrate a typical standardized bracket, illustrating by way of example an upper lateral bracket. In these figures, g designates the gingival (gum) direction, o designates the occlusal (tooth tip) direction, m designates the mesial direction and d designates the distal direction. The slot rotation angle RA, the horizontal base curvature radius $R_H$ and the slot in-out dimension IO are illustrated in FIG. 6. The slot tip angle TA1 is illustrated in FIG. 5. The slot torque angle SAI, the base curvature radius $R_V$ in the vertical plane are illustrated in FIG. 6. A slot rotation angle RA is positive if the slot is farther spaced from the tooth or bracket base at the mesial end of the bracket. The slot torque or inclination angle is positive if the slot is inclined relative to the base in the occlusal direction on the bracket. The tip angle is positive if the slot is inclined so that is more occlusal at the mesial end of the bracket. The parameters are most effective when the brackets are mounted on the teeth at specific bracket placement heights, and such heights are the distances from the maximum prominence of the tooth at which the centers of the brackets should be placed. These heights are representative of the distances from the highest tooth tip on normal size teeth. For the minority of patients with exceptionally large teeth or exceptionally small teeth, the brackets should be placed more occlusally, or less occlusally, respectively, up to 0.25–0.35 mm, and for upper incisor as much as 0.50 to 0.60 mm.

One designed, (130) the standardized brackets and archwires are manufactured for each of the different patient groups. The parameters for brackets for the Asian and Caucasian racial groups are set forth below.

For standardized brackets designed for the Asian group of patients, the above parameters are preferably as follows:

for upper centrals:
    slot in-out dimension: 0.050 inches,
    base curvature radius: infinite to –0.5 inches (concave),
    slot torque (inclination) angle: 18° to maintain wire at 11°–12°,
    slot tip angle: 4°. and
    slot rotation angle: 0°,
    placement height: 4.6 mm.

for upper laterals:
    slot in-out dimension: 0.054 inches,
    base curvature radius: 0.5 inches to infinite,
    slot inclination angle: 16° to maintain wire at 9°,
    slot tip angle: 6°. and
    slot rotation angle: –3°,
    placement height: 3.9 mm.

for upper cuspids:
    slot in-out dimension: 0.037 inches,
    base curvature radius: vert.=0.25, horiz.=0.125 inches
    slot inclination angle: 0° to maintain wire at –2° to –30°,
    slot tip angle: 8°. and
    slot rotation angle: –4°,
    placement height: 4.7 min.

for upper first bicuspids:
    slot in-out dimension: 0.042 inches,
    base curvature radius: vert.=0.125, horiz.=0.110 inches,
    slot inclination angle: 2° to maintain wire at –2°,
    slot tip angle: 4°. and
    slot rotation angle: –2°,
    placement height: 4.2 mm.

for upper second bicuspids:
    slot in-out dimension: 0.052 inches,
    base curvature radius: vert.=0.125, horiz.=0.110 inches,
    slot inclination angle: 1° to maintain wire at –3°,
    slot tip angle: 6°. and
    slot rotation angle: 0°,
    placement height: 3.6 mm.

for upper first molars:
    slot in-out dimension: 0.041 inches,
    slot inclination angle: –10° to maintain wire at –9°, slot rotation angle: 15°, and
placement height: 3.1 mm.
for upper second molars:
   slot in-out dimension: 0.041 inches,
   slot inclination angle: −10°,
   slot rotation angle: 15°, and
   placement height: 4.0 mm.
for lower centrals:
   slot in-out dimension: 0.050 inches,
   base curvature radius: vert.=0.625, horiz.=0.275 inches,
   slot inclination angle: −2° to maintain wire at −6°,
   slot tip angle: 0°. and
   slot rotation angle: 0°,
   placement height: 4.0 mm.
for lower laterals:
   slot in-out dimension: 0.050 inches,
   base curvature radius: vert.=0.625, horiz.=0.275 inches,
   slot inclination angle: 0° to maintain wire at −4°,
   slot tip angle: 0°. and
   slot rotation angle: 0°,
   placement height: 4.0 mm.
for lower cuspids:
   slot in-out dimension: 0.038 inches,
   base curvature radius: vert.=0.275, horiz.=0.125 inches,
   slot inclination angle: 0o to maintain wire at −1°,
   slot tip angle: 2°. and
   slot rotation angle: −6°,
   placement height: 4.8 mm.
for lower first bicuspids:
   slot in-out dimension: 0.045 inches,
   base curvature radius: vert.=0.275, horiz.=0.125 inches,
   slot inclination angle: −8° to maintain wire at −11°,
   slot tip angle: 3°. and
   slot rotation angle: 0°, and
   placement height: 4.0 mm.
for lower second bicuspids:
   slot in-out dimension: 0.050 inches,
   base curvature radius: vert.=0.275, horiz.=0.125 inches,
   slot inclination angle: −8° to maintain wire at −10° to −11°,
   slot tip angle: 6°. and
   slot rotation angle: 0°.
   placement height: 4.0 mm.
for lower first molars:
   slot in-out dimension: 0.041 inches,
   slot inclination angle: −10° to maintain wire at −12° to −13°,
   slot rotation angle: 2° to 4°, and
   placement height: 4.0 mm.
for lower second molars:
   slot in-out dimension: 0.041 inches,
   slot inclination angle: −7°,
   slot rotation angle: 0°, and
   placement height: 4.0 mm.

For the Asian group of patients, the parameters are preferably as stated above, but can be approximately equal to the above values, that is can deviate somewhat from the values listed above. Such deviation from the above values should nonetheless be:
   for slot inclination angle, within ±1° to 2°,
   for slot tip angle, within ±1°,
   for slot rotation angle, within ±1°,
   for slot in-out dimension, within ± a constant of 0.020 inches, which is within ±0.005 inches of being the same for all brackets, and:
      for upper lateral and second bicuspid brackets, at least 0.010 inches greater than for any upper first bicuspid and upper central brackets of the appliance, and
      for lower lateral brackets, at least 0.010 inches greater than for any lower cuspid brackets of the appliance, and
      for lower first bicuspid brackets, at least as great as the average for any lower cuspid and lower second bicuspid brackets of the appliance, and
   for base curvature radius, between ½ to 2 times the stated value, with all radii that have an absolute value of at least 0.5 inches being defined as infinite.

For standardized brackets designed for the Caucasian anthropological group of patients, the parameters are preferably as follows:
for upper centrals:
   slot in-out dimension: 0.044 inches,
   base curvature radius: vert.=0.500, horiz.=0.500,
   slot inclination angle: 15° to maintain the wire at 7° or 8°,
   slot tip angle: 5°,
   slot rotation angle: 0°,
   placement height: 4.3 mm.
for upper laterals:
   slot in-out dimension: 0.057 inches,
   base curvature radius: vert.=0.500, horiz.=0.250 inches,
   slot inclination angle: 9° to maintain the wire at 1° or 2°,
   slot tip angle: 9°,
   slot rotation angle: 4.5°,
   placement height: 3.7 mm.
for upper cuspids:
   slot in-out dimension: 0.037 inches,
   base curvature radius: vert.=0.250, horiz.=0.125 inches,
   slot inclination angle: −3° to maintain the wire at 6°,
   slot tip angle: 10°,
   slot rotation angle: 0°,
   placement height: 4.6 mm.
for upper first bicuspids:
   slot in-out dimension: 0.044 inches,
base curvature radius: vert.=0.250, horiz.=0.110 inches,
   slot inclination angle: −6° to maintain the wire at −2°,
   slot tip angle: 0°.
   slot rotation angle: 0°,
   placement height: 4.2 mm. for upper second bicuspids:
   slot in-out dimension: 0.050inches,
   base curvature radius: vert.−0.250, horiz.=0.110 inches,
   slot inclination angle: −8° to maintain the wire at −4°,
   slot tip angle: 4°.
   slot rotation angle: 0°,
   placement height: 3.6 mm.
for upper first molars:
   slot in-out dimension: 0.041 inches,
   slot inclination angle: −15° to maintain the wire at −12° or −13°,
   slot rotation angle: 15°, and
   placement height: 3.1 mm.
for upper second molars:
   slot in-out dimension: 0.041 inches, slot inclination angle: −15°,
slot rotation angle: 15°, and
placement height: 3 mm.
for lower centrals:
  slot in-out dimension: 0.045 inches,
  base curvature radius: vert.=0.625, horiz.=0.275 inches,
  slot inclination angle: −5° to maintain the wire at −1°,
  slot tip angle: 2°,
  slot rotation angle: 0°,
  placement height: 3.9 mm.
for lower laterals:
  slot in-out dimension: 0.045 inches,
  base curvature radius: vert.=0.625, horiz.=0.275 inches,
  slot inclination angle: −5° to maintain the wire at −3°,
  slot tip angle: 4°. and
  slot rotation angle: 0°,
  placement height: 3.9 mm.
for lower cuspids:
  slot in-out dimension: 0.045 inches,
  base curvature radius: vert.=0.125, horiz.=0.250 inches,
  slot inclination angle: −6° to maintain the wire at −8°,
  slot tip angle: 6°. and
  slot rotation angle: −4.5°,
  placement height: 4.7 mm.
for lower first bicuspids:
  slot in-out dimension: 0.046 inches,
  base curvature radius: 0.125, horiz.=0.250 inches,
  slot inclination angle: −7° to maintain the wire at −10° or −11°,
  slot tip angle: 3°. and
  slot rotation angle: 0°,
  placement height: 3.9 mm.
for lower second bicuspids:
  slot in-out dimension: 0.049 inches,
  base curvature radius: 0.125, horiz.=0.250 inches,
  slot inclination angle: −9° to maintain the wire at −11°,
  slot tip angle: 3°. and
  slot rotation angle: 0°.
  placement height: 3.9 mm.
for lower first molars:
  slot in-out dimension: 0.041 inches,
  slot inclination angle: −12° to maintain the wire at −17°,
  slot rotation angle: 0° to 2°, and
  placement height: 3.9 mm.
for lower second molars:
  slot in-out dimension: 0.041 inches,
  slot inclination angle: −12°,
  slot rotation angle: 4°,
  placement height: 3.9 mm.

For the Caucasian group of patients, the parameters are preferably as set forth above, but can be approximately equal to the above values, that is can deviate somewhat from the values listed above, being equal to the stated values plus or minus the same amounts stated for the Asian group appliances above.

The above listed parameter values for Asian and Caucasian patients are representative of bracket slots for wire that is nominally one mill smaller than the slot. This is commonly referred to as the full size wire. Where the small size wire is used, and where the direction of treatment movement of the tooth is generally predictable for most patients, certain parameter values, most notably in the slot inclination angle, can be changed. For Caucasian patients the values are:

| Tooth | Inclination Angle |
| --- | --- |
| upper cuspids | +2° |
| upper 1st bicus. | −10° |
| upper 2nd bicus. | −12° |
| upper 1st molars | −21° |
| lower centrals | +2° |
| lower laterals | +2° |
| lower cuspids | +2° |
| lower 1st bicus. | −2° |
| lower 2nd bicus. | −3° |
| lower 1st molars | −17° |
| lower 2nd molars | −17° |

In addition, the inclination angle figures listed above for some teeth include a component that tends to compensate for certain effects of treatment mechanics, such as inclination imposed by moments caused by rubber band treatment or some other expected step in the treatment. For example, in both the Asian and Caucasian brackets, about 4° has been added to the slot torque or inclination angle for upper incisors, about 1° for upper cuspids, and about 2° for lower cuspids.

The above data and data ranges are effective to make the standardized appliances suitable for most patients of the patient group when treated with the most likely treatment procedures.

In addition to the brackets, bracket sets, appliance and design method set forth above, an important aspect of the present invention lies in providing the appropriate appliance for patients of a particular anthropological group. While applicants' custom appliance design method can be used, as set forth by applicants in their U.S. patent application Ser. No. 07/973,973, to manufacture a custom appliance that is ideal for any particular patient, the present invention includes a method of providing orthodontic appliances particularly suitable for patients based on matching the anatomical features of the patient with the appropriate category of standardized appliance based on a correlation of the patient with the anthropological group to which the patient belongs.

In accordance with one preferred embodiment present invention, an orthodontic appliance manufacturer provides standardized sets of brackets particularly designed for treatment of patients who are of specific anthropological groups. Such standardized appliances include the Asian and Caucasian racial group specific appliances, including archwires and brackets, particularly the individual brackets and sets and subsets of brackets set forth above, and other group specific appliances designed in accordance with the statistical gathering and standardized appliance designing method described above. Such manufacturer further (142) makes available such group specific standardized appliances in such a way that information that is capable of matching a patient with one of the group specific standardized appliance groups can be correlated with the appliance provided for patients of that group. Thereby, the proper group specific standardized appliance is provided to the patient who is from that particular group, and has dental and related anatomy substantially similar to those patients from whom the data was taken in the course of the group specific standardized appliance design.

The provision of such appliances for patients according to the invention (150) may be implemented in a number of ways. In one contemplated manner of implementation, an appliance supplier, such as manufacturer or distributer of the manufacturer's products, receives an order from an orthodontist or other practitioner requesting an appliance for treatment of a patient. The orthodontist will along with or separately provide to the supplier information which can be correlate so that a matching can be made of the orthodontist's patient with an appliance or appliance component that has been designed as a standardized appliance for the group having the dental anatomy of the orthodontist's patient. Once the match is made, the appropriate appliance is supplied to the orthodontist.

The provision of such appliances may also be implemented by the supplier providing documentation or other compilation of information from which the orthodontic treatment practitioner can select the appliance based on information available to the practitioner of the patient group. For example, the manufacturer may provide a catalog that identifies various standardized orthodontic appliances as particularly suitable to patients of groups identified by name. For example, brackets having a particular geometry may be identified as suitable for patients who are Asian, who are Caucasian, or who have a particular type of malocclusion or require an extraction or other specific treatment. The suitability may be, and preferably will be, combined with the specification that the brackets are so suitable for mounting on a particular tooth of the patient of the group. The suitability may, and preferably is, combined with information that the brackets are so suitable for mounting on the teeth of the patient of the group when used in combination with other specific brackets or particular archwires. Alternatively, where specific geometric information of the standardized appliance that is appropriate for the member of the group is available to the practitioner or entity obtaining the appliance for the practitioner, the supplier may provide information of the geometric parameters of the appliance from which one possessed with the geometric parameter information needed can select the appropriate standardized appliance for the patient of the corresponding group. The supplier may, alternatively, indicate that the appropriate appliance or appliance component, such as a bracket, is designed to work with another appliance component. There are a number of ways, not limited to those set forth here, that advantages of invention can provided to patients or that the invention can be practiced.

From the above, particularly the detailed description of the invention, it will be apparent to those skilled in the art that modifications, additions and adaptations of the invention can be made without departing from the principles of the present invention.

The following is presently claimed:

1. A method of fabricating standardized orthodontic appliances for patients of a defined group of patients having similar dental anatomy, the method comprising the steps of:

for each of a plurality of individual patients, including patients who are members of the defined group, designing, with a specially programmed digital computer, a custom orthodontic appliance, the designing step including the substeps of:

digitizing tooth shape data of each of a plurality of the teeth of the individual patient for each of a plurality of patients, calculating finish positions ideal for the teeth of the individual patient by processing the digitized data, designing, from the calculated finish positions and tooth shape data, a custom orthodontic appliance for moving the teeth of the individual patient to the calculated finish positions, and for individual patients who are members of the defined group, generating a digitized record of geometric parameters of the designed custom orthodontic appliance; then, in a programmed digital computer, statistically processing data of the geometric parameters from the digitized records for patients of the defined group and generating therefrom a group standardized design of an orthodontic appliance suitable for straightening the teeth of patients of the defined group;

fabricating a standardized orthodontic appliance in accordance with the group standardized design; and producing a record of information sufficient to effectively identify the fabricated standardized orthodontic appliance as being specifically suitable for straightening the teeth of patients of the defined group.

2. The method of claim 1 wherein:

the data digitizing step includes the substep of digitizing data that includes data of the locations of a plurality of points on the surfaces of the teeth of the individual patient;

the designing step further includes the step of deriving a mathematical representation of a crown long axis of each of a plurality the teeth of the individual patient; and finish position calculating substep includes the step of calculating the finish positions that incline the teeth based on inclinations of the derived crown long axes.

3. The method of claim 1 further comprising the steps of:

determining whether a patient to be treated with a standardized appliance is a member of the defined group; and, upon determining that the patient to be treated with a standardized appliance is a member of the defined group and from the record of information, selecting the standardized appliance and providing the standardized appliance for treatment of the patient to be treated therewith.

4. The method of claim 3 further comprising the steps of:

defining the group to include patients of a selected race;

the record producing step includes the step of producing a record identifying the fabricated standardized orthodontic appliance as being specifically suitable for patients of the selected race;

determining the race of the patient to be treated with a standardized appliance; and upon determining that the patient is of the selected race, selecting and providing the standardized orthodontic appliance for treatment of the patient therewith.

5. The method of claim 3 wherein:

defining the group to include patients whose teeth are maloccluded and require orthodontic treatment; and selecting and providing the standardized orthodontic appliance for treatment of the patient therewith.

6. The method of claim 1 wherein the finish position calculating substep includes:

defining, for each dental arch, an archwire plane intersecting the teeth of the respective dental arch;

establishing, with the computer from the tooth shape data and calculated finish tooth positions, the locations of appliance connection points on the teeth of the individual patients at the intersection of the respective archwire plane with the teeth of the arch, the dental arches including a first dental arch which, where the appliance is a lingual appliance is the upper dental arch of the individual patient and otherwise is the lower dental arch of the individual patient, the archwire plane for the first dental arch being located by calculating, with the computer, the maximum overlap of the teeth of the second dental arch, establishing a clearance distance between teeth of the second arch and brackets mounted on the teeth of the first arch in the respective archwire plane.

7. A set of orthodontic brackets for Asian patients comprising:

an upper subset of upper brackets and a lower subset of lower brackets each of the subsets including a left half-subset and a right-subset;

each of the brackets for corresponding teeth of each half sub-set of the same subset being a mirror image of a corresponding bracket of the other half subset;

each of the half-subsets including a central bracket, a lateral bracket, a cuspid bracket, a first bicuspid bracket and a second bicuspid bracket;

each of the brackets having a slot and a base and being configured in accordance with dimensional parameters including a slot in-out dimension, at least one base curvature radius, a slot inclination angle, a slot tip angle and a slot rotation angle;

wherein the parameters for each bracket equal approximately:
for the upper central brackets:
slot in-out dimension: 0.050 inches,
base curvature radius: infinite
slot inclination angle: 18°,
slot tip angle: 4°. and
slot rotation angle: 0°,
for the upper lateral brackets:
slot in-out dimension: 0.054 inches,
base curvature radius: infinite,
slot inclination angle: 16°,
slot tip angle: 6°. and
slot rotation angle: −3°,
for the upper cuspid brackets:
slot in-out dimension: 0.037 inches,
base curvature radius: vert.=0.25, horiz.=0.125 inches,
slot inclination angle: 0°,
slot tip angle: 8°. and
slot rotation angle: −4°,
for the upper first bicuspid brackets:
slot in-out dimension: 0.042 inches,
base curvature radius: vert.=0.125, horiz.=0.110 inches,
slot inclination angle: 2°,
slot tip angle: 4°. and
slot rotation angle: −2°,
for the upper second bicuspid brackets:
slot in-out dimension: 0.052 inches,
base curvature radius: vert.=0.125, horiz.=0.110 inches,
slot inclination angle: 1°,
slot tip angle: 6°. and
slot rotation angle: 0°,
for the lower central brackets:
slot in-out dimension: 0.050 inches,
base curvature radius: vert.=0.625, horiz.=0.275 inches,
slot inclination angle: −2°,
slot tip angle: 0°. and
slot rotation angle: 0°,
for the lower lateral brackets:
slot in-out dimension: 0.050 inches,
base curvature radius: vert.=0.625, horiz.=0.275 inches,
slot inclination angle: 0°,
slot tip angle: 0°. and
slot rotation angle: 0°,
for the lower cuspid brackets:
slot in-out dimension: 0.038 inches,
base curvature radius: vert.=0.275, horiz.=0.125 inches,
slot inclination angle: 0°,
slot tip angle: 2°. and
slot rotation angle: −6°,
for the lower first bicuspid brackets:
slot in-out dimension: 0.045 inches,
base curvature radius: vert.=0.275, horiz.=0.125 inches,
slot inclination angle: −8°,
slot tip angle: 3°. and
slot rotation angle: 0°, and
for the lower second bicuspid brackets:
slot in-out dimension: 0.050 inches,
base curvature radius: vert.=0.275, horiz.=0.125 inches,
slot inclination angle: −8°,
slot tip angle: 6°, and
slot rotation angle: 0°; and wherein "equal approximately", for the parameters, is:
for slot inclination angle, within ±2°,
for slot tip angle, within ±1°,
for slot rotation angle, within ±1°,
for slot in-out dimension, within ± a constant of 0.020 inches, which is within ±0.005 inches of being the same for all brackets, and:
for upper lateral and second bicuspid brackets, at least 0.010 inches greater than for upper first bicuspid and upper central brackets, and
for lower lateral brackets, at least 0.010 inches greater than for lower cuspid brackets, and
for lower first bicuspid brackets, at least as great as the average for lower cuspid and lower second bicuspid brackets, and
for base curvature radius, between ½ to 2 times the stated value, with all radii that have an absolute value of at least 0.5 inches being defined as infinite.

8. The set of orthodontic brackets of claim 7 wherein:

each of the half-subsets further includes a first molar bracket and a second molar bracket; and the parameters for each molar bracket equal approximately:
for the upper first molar brackets:
slot in-out dimension: 0.041 inches,
slot inclination angle: −10°, and
slot rotation angle: 15°,
for the upper second molar brackets:
slot in-out dimension: 0.041 inches,
slot inclination angle: −10°, and
slot rotation angle: 15°,
for the lower first molar brackets:
slot in-out dimension: 0.041 inches,
slot inclination angle: −10°, and
slot rotation angle: 2° to 4°, and
for the lower second molar brackets:
slot in-out dimension: 0.041 inches,
slot inclination angle: −7°,
slot rotation angle: 0°.

9. A set of orthodontic brackets for Caucasian patients comprising:

an upper subset of upper brackets and a lower subset of lower brackets;

each of the subsets including a left half-subset and a right half-subset;

each of the brackets for corresponding teeth of each half sub-set of the same subset being a mirror image of a corresponding bracket of the other half subset;

each of the half-subsets including a central bracket, a lateral bracket, a cuspid bracket, a first bicuspid bracket and a second bicuspid bracket;

each of the brackets having a slot and a base and being configured in accordance with dimensional parameters including a slot in-out dimension, at least one base curvature radius, a slot inclination angle, a slot tip angle and a slot rotation angle;

the parameters for each bracket equaling approximately:
for the upper central brackets:
slot in-out dimension: 0.044 inches,
base curvature radius: vert.=0.500, horiz.=0.500,
slot inclination angle: 15°,
slot tip angle: 5°. and
slot rotation angle: 0°,
for the upper lateral brackets:
slot in-out dimension: 0.057 inches,
base curvature radius: vert.=0.500, horiz.=0.250 inches,
slot inclination angle: 9°,
slot tip angle: 9°. and
slot rotation angle: 4.5°,
for the upper cuspid brackets:
slot in-out dimension: 0.037 inches,
base curvature radius: vert.=0.25, horiz.=0.125 inches,
slot inclination angle: −3°,
slot tip angle: 10°. and
slot rotation angle: 0°,
for the upper first bicuspid brackets:
slot in-out dimension: 0.044 inches,
base curvature radius: vert.=0.125, horiz.=0.11 inches,
slot inclination angle: −6°,
slot tip angle: 0°. and
slot rotation angle: 0°,
for the upper second bicuspid brackets:
slot in-out dimension: 0.050 inches,
base curvature radius: vert.=0.25, horiz.=0.11 inches,
slot inclination angle: −8°,
slot tip angle: 4°. and
slot rotation angle: 0°,
for the lower central brackets:
slot in-out dimension: 0.045 inches,
base curvature radius: vert.=0.625, horiz.=0.275 inches,
slot inclination angle: −5°,
slot tip angle: 2°. and
slot rotation angle: 0°,
for the lower lateral brackets:
slot in-out dimension: 0.045 inches,
base curvature radius: vert.=0.625, horiz.=0.275 inches,
slot inclination angle: −5°,
slot tip angle: 4°. and
slot rotation angle: 0°,
for the lower cuspid brackets:
slot in-out dimension: 0.045 inches,
base curvature radius: vert.=0.275, horiz.=0.125 inches,
slot inclination angle: −6°,
slot tip angle: 6°. and
slot rotation angle: −4.5°,
for the lower first bicuspid brackets:
slot in-out dimension: 0.046 inches,
base curvature radius: vert.=0.275, horiz.=0.125 inches,
slot inclination angle: −7°,
slot tip angle: 3°. and
slot rotation angle: 0°, and
for the lower second bicuspid brackets:
slot in-out dimension: 0.049 inches,
base curvature radius: vert.=0.275, horiz.=0.125 inches,
slot inclination angle: −9°,
slot tip angle: 3°. and
slot rotation angle: 0°;
wherein "equal approximately", for the parameters, is:
for slot inclination angle, within ±2°,
for slot tip angle, within ±1°,
for slot rotation angle, within ±1°,
for slot in-out dimension, within ± a constant of 0.020 inches, which is within ±0.005 inches of being the same for all brackets, and:
for upper lateral and second bicuspid brackets, at least 0.010 inches greater than for upper first bicuspid and upper central brackets, and
for lower lateral brackets, at least 0.010 inches greater than for lower cuspid brackets, and
for lower first bicuspid brackets, at least as great as the average for lower cuspid and lower second bicuspid brackets, and
for base curvature radius, between ½ to 2 times the stated value, with all radii that have an absolute value of at least 0.5 inches being defined as infinite.

10. The set of orthodontic brackets of claim 9 wherein:

each of the half-subsets further includes a first molar bracket and a second molar bracket; and the parameters for each molar bracket equal approximately:
for the upper first molar brackets:
slot in-out dimension: 0.041 inches,
slot inclination angle: −10°, and
slot rotation angle: 15°,
for the upper second molar brackets:
slot in-out dimension: 0.041 inches,
slot inclination angle: −10°, and
slot rotation angle: 15°,
for the lower first molar brackets:
slot in-out dimension: 0.041 inches,
slot inclination angle: −10°,
slot rotation angle: 4°, and
for the lower second molar brackets:
slot in-out dimension: 0.041 inches,
slot inclination angle: −7°,
slot rotation angle: 0°.

11. A combination of brackets for an orthodontic appliance for the treatment of patients of an Asian anthropological class of patients, having similarities of dental anatomical features statistically common to the members thereof, the combination of brackets comprising:

a plurality of orthodontic brackets, each bracket having a slot and a base and being configured in accordance with dimensional parameters including a slot in-out dimension, a bracket base curvature, a slot inclination angle, a slot tip angle and a slot rotation angle, the plurality including at least two brackets, which have different combinations of dimensional parameters, selected from the group consisting of:

an upper central bracket having dimensional parameters which equal approximately the following:
  slot in-out dimension: 0.050 inches,
  base curvature radius: infinite
  slot inclination angle: 18°,
  slot tip angle: 4°. and
  slot rotation angle: 0°, an upper lateral bracket having dimensional parameters which equal approximately the following:
  slot in-out dimension: 0.054 inches,
  base curvature radius: infinite,
  slot inclination angle: 16°,
  slot tip angle: 6°. and
  slot rotation angle: −3°, an upper cuspid bracket having dimensional parameters which equal approximately the following:
  slot in-out dimension: 0.037 inches,
  base curvature radius: vert.=0.25, horiz.=0.125 inches,
  slot inclination angle: 0°,
  slot tip angle: 8°. and
  slot rotation angle: −4°, an upper first bicuspid bracket having dimensional parameters which equal approximately the following:
  slot in-out dimension: 0.042 inches,
  base curvature radius: vert.=0.125, horiz.=0.110 inches,
  slot inclination angle: 2°,
  slot tip angle: 4°. and
  slot rotation angle: −2°, an upper second bicuspid bracket having dimensional parameters which equal approximately the following:
  slot in-out dimension: 0.052 inches,
  base curvature radius: vert.=0.125, horiz.=0.110 inches,
  slot inclination angle: 1°,
  slot tip angle: 6°. and
  slot rotation angle: 0°, a lower cuspid bracket having dimensional parameters which equal approximately the following:
  slot in-out dimension: 0.038 inches,
  base curvature radius: vert.=0.275, horiz.=0.125 inches,
  slot inclination angle: 0°,
  slot tip angle: 2°. and
  slot rotation angle: −6°, a lower first bicuspid bracket having dimensional parameters which equal approximately the following:
  slot in-out dimension: 0.045 inches,
  base curvature radius: vert.=0.275, horiz.=0.125 inches,
  slot inclination angle: −8°,
  slot tip angle: 3°. and
  slot rotation angle: 0°, and a lower second bicuspid bracket having dimensional parameters which equal approximately the following:
  slot in-out dimension: 0.050 inches,
  base curvature radius: vert.=0.275, horiz.=0.125 inches,
  slot inclination angle: −8°,
  slot tip angle: 6°, and
  slot rotation angle: 0°; and wherein "equal approximately", for the parameters, is:
  for slot inclination angle, within ±2°,
  for slot tip angle, within ±1°,
  for slot rotation angle, within ±1°,
  for slot in-out dimension, within ± a constant of 0.020 inches, which is within ±0.005 inches of being the same for all of the brackets, and
  for base curvature radius, between ½ to 2 times the stated value, with all radii that have an absolute value of at least 0.5 inches being defined as infinite.

12. The combination of orthodontic brackets of claim 11 further comprising:

a molar bracket having a slot and a base and configured in accordance with dimensional parameters including a slot in-out dimension, a slot inclination angle and a slot rotation angle, and selected from the group consisting of brackets having dimensional parameters which equal approximately the following:
  for upper first molar brackets:
    slot in-out dimension: 0.041 inches,
    slot inclination angle: −10°, and
    slot rotation angle: 15°,
  for upper second molar brackets:
    slot in-out dimension: 0.041 inches,
    slot inclination angle: −10°, and
    slot rotation angle: 15°,
  for lower first molar brackets:
    slot in-out dimension: 0.041 inches,
    slot inclination angle: −10°,
    slot rotation angle: 4°, and
  for lower second molar brackets:
    slot in-out dimension: 0.041 inches,
    slot inclination angle: −7°,
    slot rotation angle: 0°.

13. The combination of orthodontic brackets of claim 11 wherein:

the plurality of brackets includes a left half-subset of brackets and a right half-subset of brackets, the brackets of each half-subset including brackets for corresponding teeth that are each a mirror image of a corresponding bracket of the other half subset;

each of the half-subsets including an upper central bracket, an upper lateral bracket, an upper cuspid bracket, an upper first bicuspid bracket and an upper second bicuspid bracket having the dimensional parameters including the slot in-out dimension, the base curvature radius, the slot inclination angle, the slot tip angle and the slot rotation angle;

the combination of brackets thereby forming a subset of brackets for an upper dental arch of a patient of the Asian class.

14. The combination of orthodontic brackets of claim 11 wherein the plurality of brackets comprises:

at least four brackets for the same bracket subset, the subset being selected from the subset group consisting of an upper subset of upper brackets and a lower subset of lower brackets;

the at least four brackets including at least two pair of brackets wherein the brackets of each pair are mirror images of each other for placement on corresponding teeth on opposite sides of a patient's mouth;

the upper subset including a pair of central brackets, a pair of lateral brackets, a pair of cuspid brackets, a pair of first bicuspid brackets and a pair of second bicuspid brackets;

the lower subset including a pair of cuspid brackets, a pair of first bicuspid brackets and a pair of second bicuspid brackets; and one bracket of each pair of the brackets having the dimensional parameters for placement on adjacent teeth.

15. The combination of orthodontic brackets of claim 14 wherein:

the at least four brackets includes at least six brackets from the same bracket subset;

the at least six brackets including at least three pair of brackets wherein the brackets of each pair are mirror images of each other for placement on corresponding teeth on opposite sides of a patients mouth; and the brackets of the at least three pair having geometric parameters designed for placement on adjacent teeth.

16. An orthodontic appliance including the combination of orthodontic brackets of claim 11, and further comprising:

an archwire having a midpoint and two ends, being symmetrical about the midpoint, and definable on each side of the midpoint by at least five adjacent sections, including, proceeding distally from the midpoint toward an end, a first section adjacent the midpoint, a second section adjacent the first section, a third section adjacent the second section, a fourth section adjacent the third section, and a fifth section adjacent the fourth section;

and wherein the plurality of brackets each has a base configured for connection to a specific one of the teeth of the patient and a slot configured to connect at a specific relative position along the archwire;

the plurality of brackets includes at least four brackets including at least two pair of brackets, each pair being configured for a different tooth and each pair including two brackets that are mirror images of each other and are configured for connection to corresponding teeth on opposite right and left sides of a dental arch of the patient; and each of the brackets being configured in accordance with the dimensional parameters that include the slot in-out dimension, the base curvature radius, the slot inclination angle, the slot tip angle and the slot rotation angle.

17. The combination of orthodontic brackets of claim 11 further comprising:

at least one bracket having a slot and a base and configured in accordance with dimensional parameters including a slot in-out dimension, a slot inclination angle and a slot rotation angle, and selected from the group consisting of brackets having dimensional parameters which equal approximately the following:

a lower central bracket having dimensional parameters which equal approximately the following:
  slot in-out dimension: 0.050 inches,
  base curvature radius: vert.=0.625, horiz.=0.275 inches,
  slot inclination angle: −2°,
  slot tip angle: 0°. and
  slot rotation angle: 0°, a lower lateral bracket having dimensional parameters which equal approximately the following:
  slot in-out dimension: 0.050 inches,
  base curvature radius: vert.=0.625, horiz.=0.275 inches,
  slot inclination angle: 0°,
  slot tip angle: 0°. and
  slot rotation angle: 0°.

18. The combination of orthodontic brackets of claim 17 wherein:

the plurality of brackets includes a left half-subset of brackets and a right half-subset of brackets, the brackets of each half-subset including brackets for corresponding teeth that are each a mirror image of a corresponding bracket of the other half subset;

each of the half-subsets including a lower central bracket, a lower lateral bracket, a lower cuspid bracket, a lower first bicuspid bracket and a lower second bicuspid bracket having the dimensional parameters including the slot in-out dimension, the base curvature radius, the slot inclination angle, the slot tip angle and the slot rotation angle;

the combination of brackets thereby forming a subset of brackets for a lower dental arch of a patient of the Asian class.

19. The combination of orthodontic brackets of claim 11 wherein:

at least two of the plurality of brackets includes at least two brackets other than an upper central bracket of the group.

20. A combination of brackets for an orthodontic appliance for the treatment of patients of a Caucasian anthropological class of patients, having similarities of dental anatomical features statistically common to the members thereof, the combination of brackets comprising:

a plurality of orthodontic brackets, each bracket having a slot and a base and being configured in accordance with dimensional parameters including a slot in-out dimension, a bracket base curvature, a slot inclination angle, a slot tip angle and a slot rotation angle, the plurality including at least two brackets, which have different combinations of dimensional parameters, selected from the group consisting of:

an upper lateral bracket having dimensional parameters which equal approximately the following:
  slot in-out dimension: 0.057 inches,
  base curvature radius: vert.=0.500, horiz.=0.250 inches,
  slot inclination angle: 9°,
  slot tip angle: 9°. and
  slot rotation angle: 4.5°, an upper first bicuspid bracket having dimensional parameters which equal approximately the following:
  slot in-out dimension: 0.044 inches,
  base curvature radius: vert.=0.125, horiz.=0.11 inches,
  slot inclination angle: −6°,
  slot tip angle: 0°. and
  slot rotation angle: 0°, an upper second bicuspid bracket having dimensional parameters which equal approximately the following:
  slot in-out dimension: 0.050 inches,
  base curvature radius: vert.=0.25, horiz.=0.11 inches,
  slot inclination angle: −8°,
  slot tip angle: 4°. and
  slot rotation angle: 0°, a lower central bracket having dimensional parameters which equal approximately the following:
  slot in-out dimension: 0.045 inches,
  base curvature radius: vert.=0.625, horiz.=0.275 inches, slot inclination angle: −5°,
slot tip angle: 2°. and
slot rotation angle: 0°,
a lower lateral bracket having dimensional parameters which equal approximately the following:
slot in-out dimension: 0.045 inches,
base curvature radius: vert.=0.625, horiz.=0.275 inches,
slot inclination angle: −5°,
slot tip angle: 4°. and
slot rotation angle: 0°,
a lower cuspid bracket having dimensional parameters which equal approximately the following:
slot in-out dimension: 0.045 inches,
base curvature radius: vert.=0.275, horiz.=0.125 inches,
slot inclination angle: −6°,
slot tip angle: 6°. and
slot rotation angle: −4.5°,
a lower first bicuspid bracket having dimensional parameters which equal approximately the following:
slot in-out dimension: 0.046 inches,
base curvature radius: vert.=0.275, horiz.=0.125 inches,
slot inclination angle: −7+,
slot tip angle: 3°. and
slot rotation angle: 0°, and
a lower second bicuspid bracket having dimensional parameters which equal approximately the following:
slot in-out dimension: 0.049 inches,
base curvature radius: vert.=0.275, horiz.=0.125 inches,
slot inclination angle: −9°,
slot tip angle: 3°. and
slot rotation angle: 0°;
wherein "equal approximately", for the parameters, is:
for slot inclination angle, within ±2°,
for slot tip angle, within ±1°,
for slot rotation angle, within ±1°,
for slot in-out dimension, within ± a constant of 0.020 inches, which is within ±0.005 inches of being the same for all brackets, and
for base curvature radius, between ½ to 2 times the stated value, with all radii that have an absolute value of at least 0.5 inches being defined as infinite.

21. The combination of orthodontic brackets of claim 20 further comprising:
a molar bracket having a slot and a base and configured in accordance with dimensional parameters including a slot in-out dimension, a slot inclination angle and a slot rotation angle, and selected from the group consisting of brackets having dimensional parameters which equal approximately the following:
for upper first molar brackets:
slot in-out dimension: 0.041 inches,
slot inclination angle: −15°, and
slot rotation angle: 15°,
for upper second molar brackets:
slot in-out dimension: 0.041 inches,
slot inclination angle: −15°, and
slot rotation angle: 15°,
for lower first molar brackets:
slot in-out dimension: 0.041 inches,
slot inclination angle: −12°,
slot rotation angle: 2°, and for lower second molar brackets:
slot in-out dimension: 0.041 inches,
slot inclination angle: −12°,
slot rotation angle: 4°.

22. The combination of claim 20 wherein:
the plurality of brackets includes a left half-subset of brackets and a right half-subset of brackets, the brackets of each half-subset including brackets for corresponding teeth that are each a mirror image of a corresponding bracket of the other half subset;
each of the half-subsets including a lower central bracket, a lower lateral bracket, a lower cuspid bracket, a lower first bicuspid bracket and a lower second bicuspid bracket having the dimensional parameters including the slot in-out dimension, the base curvature radius, the slot inclination angle, the slot tip angle and the slot rotation angle;
the combination of brackets thereby forming a subset of brackets for a lower dental arch of a patient of the Caucasian class.

23. The combination of orthodontic brackets of claim 20 wherein the plurality of brackets comprises:
at least four brackets for the same bracket subset, the subset being selected from the subset group consisting of an upper subset of upper brackets and a lower subset of lower brackets;
the at least four brackets including at least two pair of brackets wherein the brackets of each pair are mirror images of each other for placement on corresponding teeth on opposite sides of a patient's mouth;
the upper subset including a pair of lateral brackets, a pair of first bicuspid brackets and a pair of second bicuspid brackets;
the lower subset including a pair of central brackets, a pair of lateral brackets, a pair of cuspid brackets, a pair of first bicuspid brackets and a pair of second bicuspid brackets; and
one bracket of each pair of the brackets having the dimensional parameters for placement on adjacent teeth.

24. The combination of orthodontic brackets of claim 23 wherein:
the at least four brackets includes at least six brackets from the same bracket subset;
the at least six brackets including at least three pair of brackets wherein the brackets of each pair are mirror images of each other for placement on corresponding teeth on opposite sides of a patients mouth; and
the brackets of the at least three pair having geometric parameters designed for placement on adjacent teeth.

25. An orthodontic appliance including the combination of orthodontic brackets of claim 20, and further comprising:
an archwire having a midpoint and two ends, being symmetrical about the midpoint, and definable on each side of the midpoint by at least five adjacent sections, including, proceeding distally from the midpoint toward an end, a first section adjacent the midpoint, a second section adjacent the first section, a third section adjacent the second section, a fourth section adjacent the third section, and a fifth section adjacent the fourth section;
and wherein the plurality of brackets each has a base configured for connection to a specific one of the teeth of the patient and a slot configured to connect at a specific relative position along the archwire;

the plurality of brackets includes at least four brackets including at least two pair of brackets, each pair being configured for a different tooth and each pair including two brackets that are mirror images of each other and are configured for connection to corresponding teeth on opposite right and left sides of a dental arch of the patient; and each of the brackets being configured in accordance with the dimensional parameters that include the slot in-out dimension, the base curvature radius, the slot inclination angle, the slot tip angle and the slot rotation angle.

26. The combination of orthodontic brackets of claim 20 further comprising:

at least one bracket having a slot and a base and configured in accordance with dimensional parameters including a slot in-out dimension, a slot inclination angle and a slot rotation angle, and selected from the group consisting of brackets having dimensional parameters which equal approximately the following:

an upper central bracket having dimensional parameters which equal approximately the following:
slot in-out dimension: 0.044 inches,
base curvature radius: vert.=0.500, horiz.=0.500,
slot inclination angle: 15°,
slot tip angle: 5°. and
slot rotation angle: 0°; and an upper cuspid bracket having dimensional parameters which equal approximately the following:
slot in-out dimension: 0.037 inches,
base curvature radius: vert.=0.25, horiz.=0.125 inches,
slot inclination angle: -3°,
slot tip angle: 10°. and
slot rotation angle: 0°.

27. The combination of orthodontic brackets of claim 26 wherein:

the plurality of brackets includes a left half-subset of brackets and a right half-subset of brackets, the brackets of each half-subset including brackets for corresponding teeth that are each a mirror image of a corresponding bracket of the other half subset;

each of the half-subsets including an upper central bracket, an upper lateral bracket, an upper cuspid bracket, an upper first bicuspid bracket and an upper second bicuspid bracket having the dimensional parameters including the slot in-out dimension, the base curvature radius, the slot inclination angle, the slot tip angle and the slot rotation angle;

the combination of brackets thereby forming a subset of brackets for an upper dental arch of a patient of the Caucasian class.

28. The combination of orthodontic brackets of claim 20 wherein:

the at least two of the plurality of brackets includes at least two brackets other than an upper lateral bracket and other than a lower cuspid bracket of the group.

29. An orthodontic bracket for use on an upper first bicuspid in treating patients who are members of an Asian anthropological group classified on the basis of common dental anatomy, the bracket comprising:

a wire supporting structure having a base mountable on the facial side of the tooth and having an archwire slot therein having geometric parameters of a slot in-out dimension of 0.042±0.004 inches, a horizontal base curvature radius of between 1/16th and 1/4th inches and a vertical base curvature radius of between 0.055 and 0.22 inches, a slot inclination angle of 0°±2°, a slot tip angle of approximately 4°±1°, and a slot rotation angle of approximately -2±1°.

30. A method of orthodontically treating patients who are members of an Asian anthropological class of patients wherein the class is distinguished on the basis of the similarities of dental anatomical features statistically common to the members thereof, the method comprising the steps of:

identifying the patient as a member of the Asian anthropological class;

selecting a plurality of orthodontic brackets, each corresponding to a different one of the teeth of the patient;

securing the selected brackets each to the corresponding one of the teeth of the patient;

attaching an archwire to a plurality of the secured brackets orthodontically treat the teeth of the patient;

the bracket selecting step including the step of selecting orthodontic brackets, each having a slot and a base and configured in accordance with dimensional parameters including a slot in-out dimension, a base curvature radius, a slot inclination angle, a slot tip angle and a slot rotation angle, wherein the parameters the parameters for each bracket equal approximately:

for upper central brackets:
slot in-out dimension: 0.050 inches,
base curvature radius: infinite
slot inclination angle: so as to incline the archwire at 12°,
slot tip angle: 4°. and
slot rotation angle: 0°, for upper lateral brackets:
slot in-out dimension: 0.054 inches,
base curvature radius: infinite,
slot inclination angle: so as to incline the archwire at 9°,
slot tip angle: 6°. and
slot rotation angle: -3°, for upper cuspid brackets:
slot in-out dimension: 0.037 inches,
base curvature radius: vert.=0.25, horiz.=0.125 inches,
slot inclination angle: so as to incline the archwire at -3°,
slot tip angle: 8°. and
slot rotation angle: -4°, for upper first bicuspid brackets:
slot in-out dimension: 0.042 inches,
base curvature radius: vert.=0.125, horiz.=0.110 inches,
slot inclination angle: so as to incline the archwire at -2°,
slot tip angle: 4°. and
slot rotation angle: -2°, for upper second bicuspid brackets:
slot in-out dimension: 0.052 inches,
base curvature radius: vert.=0.125, horiz.=0.110 inches,
slot inclination angle: so as to incline the archwire at -3°,
slot tip angle: 6°. and
slot rotation angle: 0°, for lower central brackets:
slot in-out dimension: 0.050 inches,
base curvature radius: vert.=0.625, horiz.=0.275 inches, slot inclination angle: so as to incline the archwire at −6°,
slot tip angle: 0°. and
slot rotation angle: 0°,
for lower lateral brackets:
  slot in-out dimension: 0.050 inches,
  base curvature radius: vert.=0.625, horiz.=0.275 inches,
  slot inclination angle: so as to incline the archwire at −4°,
  slot tip angle: 0°. and
  slot rotation angle: 0°,
for lower cuspid brackets:
  slot in-out dimension: 0.038 inches,
  base curvature radius: vert.=0.275, horiz.=0.125 inches,
  slot inclination angle: so as to incline the archwire at −1°,
  slot tip angle: 2°. and
  slot rotation angle: −6°,
for lower first bicuspid brackets:
  slot in-out dimension: 0.045 inches,
  base curvature radius: vert.=0.275, horiz.=0.125 inches,
  slot inclination angle: so as to incline the archwire at −11°,
  slot tip angle: 3°. and
  slot rotation angle: 0°, and
for lower second bicuspid brackets:
  slot in-out dimension: 0.050 inches,
  base curvature radius: vert.=0.275, horiz.=0.125 inches,
  slot inclination angle: so as to incline the archwire at −10°,
  slot tip angle: 6°, and
  slot rotation angle: 0°; and
wherein "equal approximately", for the parameters, is:
  for slot inclination angle, within ±2°,
  for slot tip angle, within ±1°,
  for slot rotation angle, within ±1°,
  for slot in-out dimension, within ± a constant of 0.020 inches, which is within ±0.005 inches of being the same for all brackets, and
  for base curvature radius, between ½ to 2 times the stated value, with all radii that have an absolute value of at least 0.5 inches being defined as infinite.

31. The method of claim 30 wherein:
the archwire attaching step includes the step of selecting the archwire to have a cross sectional dimension that is nominally 0.001 inches narrower than the height of a slot in at least one of the brackets; and
the slot in the at least one of the brackets has a slot inclined at an inclination angle as follows:
  for the upper central brackets: 18°,
  for the upper lateral brackets: 16°,
  for the upper cuspid brackets: 0°,
  for the upper first bicuspid brackets: 2°,
  for the upper second bicuspid brackets: 1°,
  for the lower central brackets: −2°,
  for the lower lateral brackets: 0°,
  for the lower cuspid brackets: 0°,
  for the lower first bicuspid brackets: −8°, and
  for the lower second bicuspid brackets: −8°.

32. The method of claim 30 wherein:
the brackets selected include an upper first bicuspid bracket.

33. The method of claim 30 wherein:
the bracket selecting step includes the step of so selecting an upper first bicuspid bracket and at least one bracket selected from the group consisting of an upper cuspid bracket and an upper second bicuspid bracket.

34. The method of claim 30 wherein:
the bracket selecting step includes the step of so selecting an upper cuspid bracket, an upper first bicuspid bracket and an upper second bicuspid bracket.

35. The method of claim 30 wherein:
the bracket selecting step includes the step of so selecting an upper central bracket, an upper second bicuspid bracket, and at least one bracket selected from the group consisting of an upper lateral bracket and an upper first bicuspid bracket.

36. The method of claim 30 wherein:
the bracket selecting step includes the step of so selecting an upper central bracket, an upper second bicuspid bracket and at least two different brackets selected from the group consisting of an upper lateral bracket, an upper cuspid bracket and an upper first bicuspid bracket.

37. The method of claim 30 wherein:
the bracket selecting step includes the step of so selecting a lower central, lateral bracket, a lower cuspid bracket, a lower first bicuspid bracket and lower second bicuspid bracket.

38. The method of claim 30 wherein:
the bracket selecting step includes the step of so selecting a lower cuspid bracket.

39. The method of claim 30 wherein:
the bracket selecting step includes the step of so selecting a lower cuspid bracket, a bracket from a first group consisting of a lower central bracket and a lower lateral bracket, and a bracket from a second group consisting of a lower first bicuspid bracket and a lower second bicuspid bracket.

40. The method of claim 30 wherein:
the bracket selecting step includes the step of so selecting a lower cuspid bracket, a lower incisor bracket, a lower bicuspid bracket, and at least one different bracket selected from the group consisting of lower incisor brackets and lower bicuspid brackets.

41. The method of claim 30 wherein:
the bracket selecting step includes the step of so selecting at least two brackets for two adjacent teeth.

42. The method of claim 30 wherein:
the bracket selecting step includes the step of so selecting at least three brackets for three adjacent teeth.

43. The method of claim 30 wherein:
the bracket selecting step includes the step of so selecting at least three brackets, each for a tooth that is adjacent a tooth on which is mounted another of the three brackets.

44. The method of claim 30 wherein:
the securing step includes the step of securing the respective bracket to the corresponding one of the teeth at a distance spaced vertically from the most occlusal point of the tooth equal approximately as follows:
  for the upper central brackets: 4.6 mm,
  for the upper lateral brackets: 3.9 mm,
  for the upper cuspid brackets: 4.7 mm
  for the upper first bicuspid brackets: 3.2 mm,
  for the upper second bicuspid brackets: 3.6 mm,
  for the lower central brackets: 4.0 mm,
  for the lower lateral brackets: 4.0 mm, for the lower cuspid brackets: 4.8 mm, for the lower first bicuspid brackets: 4.0 mm, and for the lower second bicuspid brackets: 4.0 mm wherein "equal approximately" is within ±0.2.

45. The combination of orthodontic brackets of claim 30 wherein:

the at least two of the plurality of brackets includes at least two brackets other than an upper central bracket and other than an upper lateral bracket of the group.

46. The combination of orthodontic brackets of claim 30 wherein:

the at least two of the plurality of brackets includes at least two brackets other than an upper central bracket of the group.

47. A method of orthodontically treating patients who are members of an Caucasian anthropological class of patients wherein the class is distinguished on the basis of the similarities of dental anatomical features statistically common to the members thereof, the method comprising the steps of:

identifying the patient as a member of the Caucasian anthropological class;

selecting a plurality of orthodontic brackets, each corresponding to a different one of the teeth of the patient;

securing the selected brackets each to the corresponding one of the teeth of the patient;

attaching an archwire to a plurality of the secured brackets orthodontically treat the teeth of the patient;

the bracket selecting step including the step of selecting orthodontic brackets, each having a slot and a base and configured in accordance with dimensional parameters including a slot in-out dimension, a base curvature radius, a slot inclination angle, a slot tip angle and a slot rotation angle, wherein the parameters the parameters for each bracket equal approximately:

for upper lateral brackets:
slot in-out dimension: 0.057 inches,
base curvature radius: vert.=0.500, horiz.=0.250 inches,
slot inclination angle: so as to incline the archwire at 1.5°,
slot tip angle: 9°. and
slot rotation angle: 4.5°, for upper second bicuspid brackets:
slot in-out dimension: 0.050 inches,
base curvature radius: vert.=0.25, horiz.=0.11 inches,
slot inclination angle: so as to incline the archwire at −4°,
slot tip angle: 4°. and
slot rotation angle: 0°, for lower central brackets:
slot in-out dimension: 0.045 inches,
base curvature radius: vert.=0.625, horiz.=0.275 inches,
slot inclination angle: so as to incline the archwire at −1°,
slot tip angle: 2°. and
slot rotation angle: 0°, for lower lateral brackets:
slot in-out dimension: 0.045 inches,
base curvature radius: vert.=0.625, horiz.=0.275 inches,
slot inclination angle: so as to incline the archwire at −3°,
slot tip angle: 4°. and
slot rotation angle: 0°, for lower cuspid brackets:
slot in-out dimension: 0.045 inches,
base curvature radius: vert.=0.275, horiz.=0.125 inches,
slot inclination angle: so as to incline the archwire at −8°,
slot tip angle: 6°. and
slot rotation angle: −4.5°, for lower first bicuspid brackets:
slot in-out dimension: 0.046 inches,
base curvature radius: vert.=0.275, horiz.=0.125 inches,
slot inclination angle: so as to incline the archwire at −10.5°,
slot tip angle: 3°. and
slot rotation angle: 0°, and for lower second bicuspid brackets:
slot in-out dimension: 0.049 inches,
base curvature radius: vert.=0.275, horiz.=0.125 inches,
slot inclination angle: so as to incline the archwire at −11°,
slot tip angle: 3°. and
slot rotation angle: 0°;

wherein "equal approximately", for the parameters, is:
for slot inclination angle, within ±2°,
for slot tip angle, within ±1°,
for slot rotation angle, within ±1°,
for slot in-out dimension, within ± a constant of 0.020 inches, which is within ±0.005 inches of being the same for all brackets, and
for base curvature radius, between ½ to 2 times the stated value, with all radii that have an absolute value of at least 0.5 inches being defined as infinite.

48. The method of claim 47 wherein:

the archwire attaching step includes the step of selecting the archwire to have a cross sectional dimension that is nominally 0.001 inches narrower than the height of a slot in at least one of the brackets; and the slot in the at least one of the brackets has a slot inclined at an inclination angle as follows:
for the upper central brackets: 15°,
for the upper lateral brackets: 9°,
for the upper cuspid brackets: −3°,
for the upper first bicuspid brackets: −6°,
for the upper second bicuspid brackets: −8°,
for the lower central brackets: −5°,
for the lower lateral brackets: −5°,
for the lower cuspid brackets: −6°,
for the lower first bicuspid brackets: −7°, and
for the lower second bicuspid brackets: −9°.

49. The method of claim 47 wherein:

the brackets selected include an upper first bicuspid bracket.

50. The method of claim 47 wherein:

the bracket selecting step includes the step of so selecting a lower central bracket, a lower lateral bracket, a lower cuspid bracket, a lower first bicuspid bracket and lower second bicuspid bracket.

51. The method of claim 47 wherein:

the bracket selecting step includes the step of so selecting a lower cuspid bracket.

52. The method of claim 47 wherein:

the bracket selecting step includes the step of so selecting a lower cuspid bracket, a bracket from a first group consisting of a lower central bracket and a lower lateral bracket, and a bracket from a second group consisting of a lower first bicuspid bracket and a lower second bicuspid bracket.

53. The method of claim 47 wherein:

the bracket selecting step includes the step of so selecting a lower cuspid bracket, a lower incisor bracket, a lower bicuspid bracket, and at least one different bracket selected from the group consisting of lower incisor brackets and lower bicuspid brackets.

54. The method of claim 47 wherein:

the bracket selecting step includes the step of so selecting at least two brackets for two adjacent teeth.

55. The method of claim 47 wherein:

the bracket selecting step includes the step of so selecting at least three brackets for three adjacent teeth.

56. The method of claim 47 wherein:

the bracket selecting step includes the step of so selecting at least three brackets, each for a tooth that is adjacent a tooth on which is mounted another of the three brackets.

57. The method of claim 47, wherein the bracket selecting step further includes the step of selecting at least one bracket having a slot and a base and configured in accordance with dimensional parameters including a slot in-out dimension, a slot inclination angle and a slot rotation angle, from the group consisting of brackets having dimensional parameters which equal approximately the following:

for upper central brackets:
  slot in-out dimension: 0.044 inches,
  base curvature radius: vert.=0.500, horiz.=0.500,
  slot inclination angle: 15°,
  slot tip angle: 5°. and
  slot rotation angle: 0°; and for upper cuspid brackets:
  slot in-out dimension: 0.037 inches,
  base curvature radius: vert.=0.25, horiz.=0.125 inches,
  slot inclination angle: −3°,
  slot tip angle: 10°. and
  slot rotation angle: 0°.

58. The method of claim 57 wherein:

the archwire attaching step includes the step of selecting the archwire to have a cross sectional dimension that is nominally 0.003 inches narrower than the height of a slot in at least one of the brackets; and the slot in the at least one of the brackets has a slot inclined at an inclination angle as follows:
  for the upper central brackets: 15°,
  for the upper lateral brackets: 9°,
  for the upper cuspid brackets: 2°,
  for the upper first bicuspid brackets: −10°,
  for the upper second bicuspid brackets: −12°,
  for the lower central brackets: −5°,
  for the lower lateral brackets: −5°,
  for the lower cuspid brackets: 0°,
  for the lower first bicuspid brackets: −2°, and
  for the lower second bicuspid brackets: −3°.

59. The method of claim 57 wherein:

the bracket selecting step includes the step of so selecting an upper first bicuspid bracket and at least one bracket selected from the group consisting of an upper cuspid bracket and an upper second bicuspid bracket.

60. The method of claim 57 wherein:

the bracket selecting step includes the step of so selecting an upper cuspid bracket, an upper first bicuspid bracket and an upper second bicuspid bracket.

61. The method of claim 57 wherein:

the bracket selecting step includes the step of so selecting an upper central bracket, an upper second bicuspid bracket, and at least one bracket selected from the group consisting of an upper lateral bracket and an upper first bicuspid bracket.

62. The method of claim 57 wherein:

the bracket selecting step includes the step of so selecting an upper central bracket, an upper second bicuspid bracket and at least two different brackets selected from the group consisting of an upper lateral bracket, an upper cuspid bracket and an upper first bicuspid bracket.

63. The method of claim 57 wherein:

the securing step includes the step of securing the respective bracket to the corresponding one of the teeth at a distance spaced vertically from the most occlusal point of the tooth equal approximately as follows:
  for the upper central brackets: 4.3 mm,
  for the upper lateral brackets: 3.7 mm,
  for the upper cuspid brackets: 4.6 mm
  for the upper first bicuspid brackets: 4.2 mm,
  for the upper second bicuspid brackets: 3.6 mm,
  for the lower central brackets: 3.9 mm,
  for the lower lateral brackets: 3.9 mm,
  for the lower cuspid brackets: 4.7 mm,
  for the lower first bicuspid brackets: 3.9 mm, and
  for the lower second bicuspid brackets: 3.9 mm wherein "equal approximately" is within ±0.2.

64. A method of providing an orthodontic appliance for the treatment of patients of an Asian anthropological class of patients, having similarities of dental anatomical features statistically common to the members thereof, comprising the steps of:

providing a plurality of orthodontic brackets, each bracket having a slot and a base and being configured in accordance with dimensional parameters including a slot in-out dimension, a bracket base curvature, a slot inclination angle, a slot tip angle and a slot rotation angle, the plurality including at least two brackets which have different combinations of dimensional parameters, the plurality being selected from the group consisting of brackets having dimensional parameters which equal approximately the following:

for upper central brackets:
  slot in-out dimension: 0.050 inches,
  base curvature radius: infinite
  slot inclination angle: 18°,
  slot tip angle: 4°. and
  slot rotation angle: 0°, for upper lateral brackets:
  slot in-out dimension: 0.054 inches,
  base curvature radius: infinite,
  slot inclination angle: 16°,
  slot tip angle: 6°. and
  slot rotation angle: −3°, for upper cuspid brackets:
  slot in-out dimension: 0.037 inches,
  base curvature radius: vert.=0.25, horiz.=0.125 inches,
  slot inclination angle: 0°,
  slot tip angle: 8°. and
  slot rotation angle: −4°, for upper first bicuspid brackets:
  slot in-out dimension: 0.042 inches,
  base curvature radius: vert.=0.125, horiz.=0.110 inches, slot inclination angle: 2°,
slot tip angle: 4°. and
slot rotation angle: −2°,
for upper second bicuspid brackets:
slot in-out dimension: 0.052 inches,
base curvature radius: vert.=0.125, horiz.=0.110 inches,
slot inclination angle: 1°,
slot tip angle: 6°. and
slot rotation angle: 0°,
for lower central brackets:
slot in-out dimension: 0.050 inches,
base curvature radius: vert.=0.625, horiz.=0.275 inches,
slot inclination angle: −2°,
slot tip angle: 0°. and
slot rotation angle: 0°,
for lower lateral brackets:
slot in-out dimension: 0.050 inches,
base curvature radius: vert.=0.625, horiz.=0.275 inches,
slot inclination angle: 0°,
slot tip angle: 0°. and
slot rotation angle: 0°,
for lower cuspid brackets:
slot in-out dimension: 0.038 inches,
base curvature radius: vert.=0.275, horiz.=0.125 inches,
slot inclination angle: 0°,
slot tip angle: 2°. and
slot rotation angle: −6°,
for lower first bicuspid brackets:
slot in-out dimension: 0.045 inches,
base curvature radius: vert.=0.275, horiz.=0.125 inches,
slot inclination angle: −8°,
slot tip angle: 320 . and
slot rotation angle: 0°, and
for lower second bicuspid brackets:
slot in-out dimension: 0.050 inches,
base curvature radius: vert.=0.275, horiz.=0.125 inches,
slot inclination angle: −8°,
slot tip angle: 6°, and
slot rotation angle: 0°; and
wherein "equal approximately", for the parameters, is:
for slot inclination angle, within ±2°,
for slot tip angle, within ±1°,
for slot rotation angle, within ±1°,
for slot in-out dimension, within ± a constant of 0.020 inches, which is within ±0.005 inches of being the same for all brackets, and
for base curvature radius, between ½ to 2 times the stated value, with all radii that have an absolute value of at least 0.5 inches being defined as infinite; and
identifying the brackets for treatment of patients who are members of the Asian anthropological class of patients.

65. The method of claim 64 wherein:
the plurality of brackets so provided includes an upper bicuspid bracket selected from the group.

66. The method of claim 64 wherein:
the plurality of brackets so provided includes an upper bicuspid bracket selected from the group and at least one bracket from the group is selected from the sub-group thereof consisting of an upper cuspid bracket and an upper second bicuspid bracket.

67. The method of claim 64 wherein:
the plurality of brackets so provided includes an upper cuspid bracket, an upper first bicuspid bracket and an upper second bicuspid bracket.

68. The method of claim 64 wherein:
the plurality of brackets so provided includes an upper central bracket, an upper second bicuspid bracket, and at least one bracket selected from a sub-group of the group consisting of an upper lateral bracket, an upper cuspid bracket and an upper first bicuspid bracket.

69. The method of claim 64 wherein:
the plurality of brackets so provided includes an upper central bracket, an upper second bicuspid bracket, and at least two different brackets selected from a sub-group of the group consisting of an upper lateral bracket, an upper cuspid bracket and an upper first bicuspid bracket.

70. The method of claim 64 wherein:
the plurality of brackets so provided includes a lower central bracket, a lower lateral bracket, a lower cuspid bracket, a lower first bicuspid bracket and a lower second bicuspid bracket.

71. The method of claim 64 wherein:
the plurality of brackets so provided includes a lower cuspid bracket.

72. The method of claim 64 wherein:
the plurality of brackets so provided includes a lower cuspid bracket, a bracket selected from a first sub-group of the group consisting of a lower central bracket and a lower lateral bracket, and a bracket selected from a second subgroup of the group consisting of a lower first bicuspid bracket and a lower second bicuspid bracket.

73. The method of claim 64 wherein:
the plurality of brackets so provided includes a lower cuspid bracket, a first anterior bracket selected from a first sub-group of the group consisting of a lower central bracket and a lower lateral bracket, a first posterior bracket selected from a second subgroup of the group consisting of a lower first bicuspid bracket and a lower second bicuspid bracket, and at least one bracket different from the first anterior and first posterior brackets and selected from a third subgroup of the group consisting of the brackets of the first and second subgroups.

74. The method of claim 64 further comprising:
providing an additional bracket in the form of a buccal tube having a mounting band, the additional bracket having a slot and a base and being configured with dimensional parameters of a slot in-out dimension, a slot inclination angle and a slot rotation angle, the additional bracket being selected from the group consisting of brackets having dimensional parameters which equal approximately the following:
for upper first molar brackets:
slot in-out dimension: 0.041 inches,
slot inclination angle: −10°, and
slot rotation angle: 15°,
for upper second molar brackets:
slot in-out dimension: 0.041 inches,
slot inclination angle: −10°, and
slot rotation angle: 15°,
for lower first molar brackets:
slot in-out dimension: 0.041 inches,
slot inclination angle: −10°, and
slot rotation angle: 4°, and
for lower second molar brackets:

slot in-out dimension: 0.041 inches,
slot inclination angle: −7°,
slot rotation angle: 0°.

75. A method of providing an orthodontic appliance for the treatment of patients of an Caucasian anthropological class of patients, having similarities of dental anatomical features statistically common to the members thereof, comprising the steps of:

providing a plurality of orthodontic brackets, each bracket having a slot and a base and being configured in accordance with dimensional parameters including a slot in-out dimension, a bracket base curvature, a slot inclination angle, a slot tip angle and a slot rotation angle, the plurality including at least two brackets which have different combinations of dimensional parameters, the plurality being selected from the group consisting of brackets having dimensional parameters which equal approximately the following:

for upper lateral brackets:
slot in-out dimension: 0.057 inches,
base curvature radius: vert.=0.500, horiz.=0.250 inches,
slot inclination angle: 9°,
slot tip angle: 9°. and
slot rotation angle: 4.5°, for upper first bicuspid brackets:
slot in-out dimension: 0.044 inches,
base curvature radius: vert.=0.125, horiz.=0.11 inches,
slot inclination angle: −6°,
slot tip angle: 0°. and
slot rotation angle: 0°, for upper second bicuspid brackets:
slot in-out dimension: 0.050 inches,
base curvature radius: vert.=0.25, horiz.=0.11 inches,
slot inclination angle: −8°,
slot tip angle: 4°. and
slot rotation angle: 0°, for lower central brackets:
slot in-out dimension: 0.045 inches,
base curvature radius: vert.=0.625, horiz.=0.275 inches,
slot inclination angle: −5°,
slot tip angle: 2°. and
slot rotation angle: 0°, for lower lateral brackets:
slot in-out dimension: 0.045 inches,
base curvature radius: vert.=0.625, horiz.=0.275 inches,
slot inclination angle: −5°,
slot tip angle: 4°. and
slot rotation angle: 0°, for lower cuspid brackets:
slot in-out dimension: 0.045 inches,
base curvature radius: vert.=0.275, horiz.=0.125 inches,
slot inclination angle: −6°,
slot tip angle: 6°. and
slot rotation angle: −4.5°, for lower first bicuspid brackets:
slot in-out dimension: 0.046 inches,
base curvature radius: vert.=0.275, horiz.=0.125 inches,
slot inclination angle: −7+,
slot tip angle: 3°. and
slot rotation angle: 0°, and for lower second bicuspid brackets:
slot in-out dimension: 0.049 inches,
base curvature radius: vert.=0.275, horiz.=0.125 inches,
slot inclination angle: −9°,
slot tip angle: 3°. and
slot rotation angle: 0°;

wherein "equal approximately", for the parameters, is:
for slot inclination angle, within ±2°,
for slot tip angle, within ±1°,
for slot rotation angle, within ±1°,
for slot in-out dimension, within ± a constant of 0.020 inches, which is within ±0.005 inches of being the same for all brackets, and for base curvature radius, between ½ to 2 times the stated value, with all radii that have an absolute value of at least 0.5 inches being defined as infinite.

76. The method of claim 75 wherein:
the bracket providing step includes the step of identifying the brackets for treatment of patients who are members of the Caucasian anthropological class of patients.

77. The method of claim 75 wherein:
the plurality of brackets so provided includes an upper bicuspid bracket selected from the group.

78. The method of claim 74 wherein:
the plurality of brackets so provided includes a lower central bracket, a lower lateral bracket, a lower cuspid bracket, a lower first bicuspid bracket and a lower second bicuspid bracket.

79. The method of claim 74 wherein:
the plurality of brackets so provided includes a lower cuspid bracket.

80. The method of claim 75 wherein:
the plurality of brackets so provided includes a lower cuspid bracket, a bracket selected from a first subgroup of the group consisting of a lower central bracket and a lower lateral bracket, and a bracket selected from a second subgroup of the group consisting of a lower first bicuspid bracket and a lower second bicuspid bracket.

81. The method of claim 75 wherein:
the plurality of brackets so provided includes a lower cuspid bracket, a first anterior bracket selected from a first sub-group of the group consisting of a lower central bracket and a lower lateral bracket, a first posterior bracket selected from a second subgroup of the group consisting of a lower first bicuspid bracket and a lower second bicuspid bracket, and at least one bracket different from the first anterior and first posterior brackets and selected from a third subgroup of the group consisting of the brackets of the first and second subgroups.

82. The method of claim 75 further comprising:
providing an additional bracket in the form of a buccal tube having a mounting band, the additional bracket having a slot and a base and being configured with dimensional parameters of a slot in-out dimension, a slot inclination angle and a slot rotation angle, the additional bracket being selected from the group consisting of brackets having dimensional parameters which equal approximately the following:

for upper first molar brackets:
slot in-out dimension: 0.041 inches,
slot inclination angle: −15°, and
slot rotation angle: 15°, for upper second molar brackets:
slot in-out dimension: 0.041 inches, slot inclination angle: −15°, and
slot rotation angle: 15°,
for lower first molar brackets:
    slot in-out dimension: 0.041 inches,
    slot inclination angle: −12°,
    slot rotation angle: 2°, and
for lower second molar brackets:
    slot in-out dimension: 0.041 inches,
    slot inclination angle: −12°,
    slot rotation angle: 4°.

83. The method of claim 75 wherein the step of providing a plurality of brackets further includes the step of providing at least one bracket having a slot and a base and configured in accordance with dimensional parameters including a slot in-out dimension, a slot inclination angle and a slot rotation angle, from the group consisting of brackets having dimensional parameters which equal approximately the following:
for upper central brackets:
    slot in-out dimension: 0.044 inches,
    base curvature radius: vert.=0.500, horiz.=0.500,
    slot inclination angle: 15°,
    slot tip angle: 5°. and
    slot rotation angle: 0°; and
for upper cuspid brackets:
    slot in-out dimension: 0.037 inches,
    base curvature radius: vert.=0.25, horiz.=0.125 inches,
    slot inclination angle: −3°,
    slot tip angle: 10°. and
    slot rotation angle: 0°.

84. The method of claim 83 wherein:
the plurality of brackets so provided includes an upper bicuspid bracket selected from the group and at least one bracket from the group is selected from the sub-group thereof consisting of an upper cuspid bracket and an upper second bicuspid bracket.

85. The method of claim 83 wherein:
the plurality of brackets so provided includes an upper cuspid bracket, an upper first bicuspid bracket and an upper second bicuspid bracket.

86. The method of claim 83 wherein:
the plurality of brackets so provided includes an upper central bracket, an upper second bicuspid bracket, and at least one bracket selected from a sub-group of the group consisting of an upper lateral bracket, an upper cuspid bracket and an upper first bicuspid bracket.

87. The method of claim 83 wherein:
the plurality of brackets so provided includes an upper central bracket, an upper second bicuspid bracket, and at least two different brackets selected from a sub-group of the group consisting of an upper lateral bracket, an upper cuspid bracket and an upper first bicuspid bracket.

88. A method of orthodontics for correcting malocclusions of a patient with an orthodontic appliance, the method comprising the steps of:
manufacturing a set of orthodontic brackets and an orthodontic archwire specifically configured for placement on, and correcting malocclusions of, the teeth of persons of a given ethnic race; and
determining the ethnic race of the patient, and, in response to a determination that the patient is of the given ethnic race:
    selecting the brackets for placement on the teeth of the patient, and
    selecting the archwire for attachment to the brackets.

89. The method of claim 88 wherein:
the bracket manufacturing step includes the step of manufacturing a plurality of brackets whose configurations each include the depth and angulation of a groove derived from a mathematical archform model of persons of the given ethnic race.

90. A set of orthodontic brackets for treating patients of a given ethnic race, the brackets being manufactured by a process comprising the steps of:
designing a plurality of orthodontic brackets, each having a base portion configured and adapted for attachment to a particular tooth of persons of a given ethnic race, and each having an archwire support portion fixed to the base portion;
designing a groove for receiving an archwire in each archwire support portion, the groove having a depth and an angulation specifically selected to correct malocclusions of the teeth of persons of the given ethnic race; and
manufacturing each of the designed brackets having the respective designed groove therein.

91. The set of brackets of claim 90 wherein:
the bracket manufacturing step includes the step of manufacturing brackets with the aid of a specially programmed digital computer programmed to control the production of brackets as designed for attachment of each to a particular tooth of persons of the given ethnic race to correct malocclusions of said teeth.

92. The set of brackets of claim 91 wherein the designing steps include the steps of:
designing, with the aid of the computer, custom orthodontic brackets and grooves therefor to specifically correct malocclusions of a plurality of individual persons of the given ethnic race; and
statistically analyzing the designed custom orthodontic brackets and deriving thereby configurations of standard brackets for persons of the given ethnic race.

93. The set of brackets of claim 91 wherein:
the designing steps include the step of designing the brackets and grooves therefor by analyzing, with the computer, data derived from the dental anatomies of persons of the given ethnic race based on a mathematical model for the teeth of persons of the given ethnic race.

94. The set of brackets of claim 93 wherein:
the method includes the steps of digitizing the data to represent the shapes of the teeth and jaws of persons of the given ethnic race and designing the brackets from the digitized data.

95. The set of brackets of claim 90 wherein:
the designing steps are based on ideal crown long axis inclination angles and jaw shape characteristic of persons of the given ethnic race.

96. An orthodontic appliance comprising the set of brackets of claim 90 and further comprising:
an orthodontic archwire manufactured according to the process of:
    designing an orthodontic archwire having an arcuate shape configured to fit in each of the grooves of the brackets, when the brackets are attached on the teeth of the persons of the given ethnic race, and to correct malocclusions of the teeth of persons of the given ethnic race; and
    manufacturing the archwire in accordance with the archwire design.

97. The set of brackets of claim 90 wherein:
the designing step includes the step of designing the brackets configured to fit on, and correct malocclusions of, the teeth of persons of the given ethnic race whose teeth are maloccluded.

98. The set of brackets of claim 90 wherein: the designing step includes the steps of:

measuring parameters of the teeth of persons of the same ethnic group, each of which require substantial orthodontic work to correct malocclusions, computing correct finish positions of the teeth of each of the patients of the group and, for each patient, the configurations of brackets and archwires for moving the teeth of the patient to the correct finish positions, and averaging the computed parameters; and the manufacturing step includes the step of manufacturing brackets the brackets to the averaged computed parameters.

99. An orthodontic appliance for treating patients of a given ethnic race, the appliance comprising a plurality of brackets each having a groove therein and an orthodontic archwire manufactured according to the process of:

designing an orthodontic archwire having an arcuate shape configured to fit in each of the grooves of the brackets, when the brackets are attached on the teeth of the persons of the given ethnic race, and to correct malocclusions of the teeth of persons of the given ethnic race; and manufacturing the archwire in accordance with the archwire design.

100. The appliance of claim 99 further comprising a set of orthodontic brackets for treating patients of the given ethnic race, the brackets being manufactured by a process comprising the steps of:

designing a plurality of orthodontic brackets, each having a base portion configured and adapted for attachment to a particular tooth of persons of a given ethnic race, and each having an archwire support portion fixed to the base portion;

designing a groove for receiving the archwire in each archwire support portion, the groove having a depth and an angulation specifically selected to correct malocclusions of the teeth of persons of the given ethnic race; and manufacturing each of the designed brackets having the respective designed groove therein.

101. A plurality of brackets each having a base portion and a face portion;

with each of the base portions having a configuration determined according to the method comprising a step of adapting the base portions for attachment to a particular tooth of an individual of a particular ethnic race;

and with each of the face portions having a groove for receiving an archwire wherein the depth and orientation of the groove are determined by the method comprising a step of specifically selecting the depth and orientation for treatment of persons of the particular ethnic race of the individual.

102. The plurality of brackets claim 101 wherein:

each of the base portions has a configuration determined according to the method comprising a step of adapting the base portions for attachment to a particular tooth of an individual of the Asian race;

and each of the face portions has a groove for receiving an archwire wherein the depth and orientation of the groove are determined according to the method comprising a step of calculating the depth and orientation to move the teeth toward an ideal dental archform for an individual of the Asian race.

103. The plurality of brackets claim 101 wherein:

wherein the configuration of each of the base portions and the depth and orientation of each face portion are determined according to the method comprising a step of deriving the depth and orientation from a mathematical archform model established for a particular ethnic race.

104. The plurality of brackets claim 101 wherein:

the configuration of each of the base portions and the depth and orientation of each face portion are determined according to a method comprising a step of deriving the depth and configuration from a mathematical archform model established for a particular ethnic race; and the archform model is determined with the aid of a digital computer programmed to produce a digitized mathematical archform models.

105. The plurality of brackets claim 101 wherein:

wherein the configuration of each of the base portions and the depth and orientation of each face portion are determined according to a method comprising a step of deriving the configuration of the base portions and the depth and orientation of each face portion from measurements of the shapes of the teeth of individuals of the same ethnic race as the patient.

106. The plurality of brackets claim 101 wherein:

wherein the configuration of each of the base portions and the depth and orientation of each face portion are determined according to a method comprising a step of deriving the configuration of each of the base portions and the depth and orientation of each face portion from measurements of points on the surfaces of the teeth of individuals of the same ethnic race as the patient and a calculation of inclinations of the crown long axes of the teeth of such individuals, the points including labial-lingually spaced points at the tooth gum intersections of the teeth and labial-lingually spaced points at the occlusal ends of the teeth.

107. An orthodontic appliance comprising the plurality of brackets claim 101 and further comprising:

an orthodontic archwire configured for connection to each of the brackets to move the teeth of the patient to finish positions determined according to a method comprising a step of specially determining the finish positions that are ideal for patients of the particular ethnic race.

108. A method of orthodontics for correcting malocclusions comprising the steps of:

a. determining the ethnic race of the patient, b. selecting for placement on the teeth of the patient brackets designed solely for use on an individual of the same ethnic race as the patient, c. selecting for attachment to the brackets an archwire designed solely for use with said brackets.

109. The method of claim 108 wherein:

the bracket selecting step includes the step of selecting for placement on the teeth of the patient brackets each having an archwire receiving groove thereon and each having a configuration including depth and angulation of the groove on the bracket derived from a mathematical archform model of an individual of the same ethnic race as the patient.

* * * * *

UNITED STATES PATENT AND TRADEMARK OFFICE
CERTIFICATE OF CORRECTION

PATENT NO. : 5,533,895
DATED : July 9, 1996
INVENTOR(S) : Craig A. Andreiko, et al.

It is certified that error appears in the above-indentified patent and that said Letters Patent is hereby corrected as shown below:

In claim 2 at column 22, line 25, before finish, insert --the--.

In claim 7 at column 23, line 13, after right, insert --half---.

In claim 19, column 30, line 22, before at, insert --the--.

In claim 26 at column 31, line 25, delete "-7+" and insert --7°--.

In claim 64 at column 41, line 36, delete "320" and insert --3°--.

Signed and Sealed this

Twenty-second Day of July, 1997

*Attest:*

BRUCE LEHMAN

*Attesting Officer*  Commissioner of Patents and Trademarks